(12) United States Patent
Hagiwara et al.

(10) Patent No.: US 12,023,338 B2
(45) Date of Patent: Jul. 2, 2024

(54) PHARMACEUTICAL COMPOSITION AND TREATMENT METHOD FOR GENETIC DISEASE ASSOCIATED WITH SPLICING ABNORMALITIES

(71) Applicant: KYOTO UNIVERSITY, Kyoto (JP)

(72) Inventors: Masatoshi Hagiwara, Kyoto (JP); Masahiko Ajiro, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 445 days.

(21) Appl. No.: 17/210,874

(22) Filed: Mar. 24, 2021

(65) Prior Publication Data

US 2021/0205314 A1 Jul. 8, 2021

Related U.S. Application Data

(62) Division of application No. 16/486,980, filed as application No. PCT/JP2018/006070 on Feb. 20, 2018, now abandoned.

(30) Foreign Application Priority Data

Feb. 20, 2017 (JP) ................................. 2017-029306

(51) Int. Cl.

| | |
|---|---|
| *A61K 31/519* | (2006.01) |
| *A61K 31/428* | (2006.01) |
| *A61K 31/437* | (2006.01) |
| *A61K 31/443* | (2006.01) |
| *A61K 31/4439* | (2006.01) |
| *A61K 31/4709* | (2006.01) |
| *A61K 31/52* | (2006.01) |
| *A61K 31/5377* | (2006.01) |
| *A61K 31/55* | (2006.01) |
| *A61P 11/00* | (2006.01) |
| *A61P 43/00* | (2006.01) |

(52) U.S. Cl.
CPC ............ *A61K 31/52* (2013.01); *A61K 31/428* (2013.01); *A61K 31/437* (2013.01); *A61K 31/443* (2013.01); *A61K 31/4439* (2013.01); *A61K 31/4709* (2013.01); *A61K 31/519* (2013.01); *A61K 31/5377* (2013.01); *A61K 31/55* (2013.01); *A61P 11/00* (2018.01); *A61P 43/00* (2018.01)

(58) Field of Classification Search
CPC ..... A61K 31/428; A61K 31/52; A61K 31/519
See application file for complete search history.

(56) References Cited

U.S. PATENT DOCUMENTS

| | | | |
|---|---|---|---|
| 9,273,364 B2 | 3/2016 | Hagiwara et al. | |
| 9,745,323 B2 | 8/2017 | Hagiwara | |
| 2006/0183909 A1 | 8/2006 | Schmitt et al. | |
| 2013/0102644 A1 | 4/2013 | Hagiwara et al. | |
| 2015/0018297 A1 | 1/2015 | Jo et al. | |
| 2015/0225421 A1 | 8/2015 | Hagiwara et al. | |
| 2016/0152620 A1 | 6/2016 | Hagiwara et al. | |
| 2016/0303089 A1 | 10/2016 | Hagiwara et al. | |
| 2018/0118748 A1 | 5/2018 | Slaugenhaupt et al. | |
| 2018/0133208 A1 | 5/2018 | Cardelli et al. | |
| 2018/0258090 A1 | 9/2018 | Van de Bittner et al. | |

FOREIGN PATENT DOCUMENTS

| | | | |
|---|---|---|---|
| CN | 102727499 A | 10/2012 | |
| EP | 3 020 829 A1 | 5/2016 | |
| JP | 2005-132834 A | 5/2005 | |
| WO | WO 2007/062028 A2 | 5/2007 | |
| WO | WO 2010/010797 A1 | 1/2010 | |
| WO | WO 2010/011642 A2 | 1/2010 | |
| WO | WO 2010/118367 A2 | 10/2010 | |
| WO | WO 2011/152043 A | 12/2011 | |
| WO | WO 2012/001941 A1 | 1/2012 | |
| WO | WO 2014/021337 A1 | 2/2014 | |
| WO | WO 2014/083327 A1 | 6/2014 | |
| WO | WO 2015/005491 A1 | 1/2015 | |
| WO | WO-2015005491 A1 * | 1/2015 | ............. A61K 31/52 |
| WO | WO 2015/083750 A1 | 6/2015 | |
| WO | WO 2016/011394 A1 | 1/2016 | |

(Continued)

OTHER PUBLICATIONS

De Nocochea-Campion et al., J of Hematology & Oncology, 2016, vol. 9(85), pp. 1-9. (Year: 2016).*
Anderson, Amy. Chemistry & Biology 2003, vol. 10, pp. 787-797. (Year: 2003).*
Thiel, Karl. Nature Biotechnology 2004, vol. 22(5), pp. 513-519. (Year: 2004).*
Translation of p. 6 of WO2015005491, published Jan. 15, 2015. (Year: 2023).*
Extended European Search Report issued Apr. 8, 2021, in European Patent Application No. 18754512.4.

(Continued)

*Primary Examiner* — Amy L Clark
*Assistant Examiner* — Janet L Coppins
(74) *Attorney, Agent, or Firm* — Birch, Stewart, Kolach & Birch, LLP

(57) ABSTRACT

A pharmaceutical composition for genetic diseases caused by an aberrant splicing regulation is provided. Provided are a pharmaceutical composition for preventing, ameliorating, suppressing progression of, and/or treating the genetic diseases caused by an aberrant splicing regulation, the pharmaceutical composition containing, as an active ingredient, a compound capable of suppressing an aberrant splicing regulation that contributes to the development or progression of genetic diseases caused by an aberrant splicing regulation, and a method for preventing, ameliorating, suppressing progression of, and/or treating the genetic diseases using a compound capable of suppressing an aberrant splicing regulation that contributes to the development or progression of genetic diseases caused by an aberrant splicing regulation.

6 Claims, 6 Drawing Sheets

(56) References Cited

FOREIGN PATENT DOCUMENTS

| WO | WO 2016/075333 A1 | 5/2016 |
|---|---|---|
| WO | WO 2016/115434 A1 | 7/2016 |
| WO | WO 2016/179481 A1 | 11/2016 |
| WO | WO 2017/175842 A1 | 10/2017 |
| WO | WO 2017/182581 A1 | 10/2017 |
| WO | WO 2017/220315 A1 | 12/2017 |

OTHER PUBLICATIONS

Office Action issued Mar. 24, 2021, in Chinese Patent Application No. 201880011889.
Anderson, A., Chemistry & Biology (2003), vol. 10, pp. 787-797.
Asahi et al., "Naturally- and experimentally-designed restorations of the Parkin gene deficit in autosomal recessive juvenile parkinsonism," Biochemical and Biophysical Research Communications (2010), vol. 391, pp. 800-805.
Avsar et al., "Adenosine acting via AI receptors, controls the transition to status epilepticus-like behaviour in an in vitro model of epilepsy," Neuropharmacology, 2004, vol. 47, No. 3, pp. 427-437.
Chimenti et al., "Prevalence of Fabry Disease in Female Patients With Late-Onset Hypertrophic Cardiomyopathy," Circulation 110, 2004, pp. 1047-1053.
Herrendorff et al., "Identification of Plant-derived Alkaloids with Therapeutic Potential for Myotonic Dystrophy Type I," J Biol Chem, 2016, vol. 291, No. 33, pp. 17165-17177.
Hwu et al., "Newborn Screening for Fabry Disease in Taiwan Reveals a High Incidence of the Later-Onset GLA Mutation c.936+9196>A (IVS4+919G>A)," Human Mutation 30(10), 2010, pp. 1397-1405.
International Search Report (PCT/ISA/210) issued in PCT/JP2018/006070, dated May 15, 2018.
Lin et al., High Incidence of the Cardiac Variant of Fabry Disease Revealed by Newborn Screening in the Taiwan Chinese Population, Circ Cardiovasc Genet 2(5) 2009, pp. 450-456.
Mariano et al., "Systematic diversification of benzylidene heterocycles yields novel inhibitor scaffolds selective for Dyrk1A, Clk1 and CK2," European journal of Medicinal Chemistry, 2016, vol. 112, pp. 209-216.
Meijer et al., J. Innate Immun. (2016), vol. 8, pp. 330-349.
Muraki et al., "Manipulation of Alternative Splicing by a Newly Developed Inhibitor of Clks," J Biol Chem, 2004, vol. 279, No. 23, pp. 24246-24254.
Nakao et al., "An Atypical Variant of Fabry's Disease in Men with Left Ventricular Hypertrophy," The New England Journal of Medicine, 1995, vol. 333, pp. 288-293.
Ohe et al., "Modulation of Alternative Splicing with Chemical Compounds in New Therapeutics for Human Diseases," ACS Chem Biol, 2015, vol. 10, No. 4, pp. 914-924.
Ohe et al., "Modulation of Alternative Splicing with Chemical Compounds in New Therapeutics for Human Diseases," ACS Chem. Bio. (2015), vol. 10, No. 4, pp. 914-924.
Partial Supplementary European Search Report issued Dec. 4, 2020, in European Patent Application No. 18754512.4.
Sachdev et al., "Prevalence of Anderson-Fabry Disease in Male Patients With Late Onset Hypertrophic Cardiomyopathy," Circulation 105, 2002, pp. 1407-1411.
Shetty et al., "Specific correction of a splice defect in brain by nutritional supplementation," Human Molecular Genetics, 2011, vol. 20, No. 21, pp. 4093-4101.
Tazi et al., Biochimica et Biophysica Acta (2009), vol. 1792, pp. 14-26.
Wang et al., "Composition, standardization and chemical profiling of Banisteriopsis caapi, a plant for the treatment of neurodegenerative disorders relevant to Parkinson's disease," Journal of Ethnopharmacology, 2010, vol. 128, No. 3, pp. 662-671.
Wood et al., "RNA-targeted splice-correction therapy for neuromuscular disease," Brain (2010), vol. 133, pp. 957-972.
Written Opinion of the International Searching Authority (PCT/ISA/237) issued in PCT/JP2018/006070 dated May 15, 2018.
Yang et al., "S-adenosylmethionine and Its Metabolite Induce Apoptosis in HepG2 Cells: Role of Protein Phosphatase 1 and Bcl-xs," Hepatology, 2004, vol. 40, No. 1, pp. 221-231.
Yoshida et al., "Rectifier of aberrant mRNA splicing recovers tRNA modification in familial dysautonomia," PNAS, 2015, vol. 112, No. 9, pp. 2764-2769.
Thiel, Karl, "Structure-aided drug design's next generation," Nature Biotechnology (2004), vol. 22, No. 5, pp. 513-519.
Chinese Office Action and Search Report for Chinese Application No. 202210073788.3, dated Aug. 7, 2023, with an English translation.

* cited by examiner

1) Exon skipping type

2) Splice site selection type

3) Intron retention type

4) Pseudo-exon type

PHARMACEUTICAL COMPOSITION AND TREATMENT METHOD FOR GENETIC DISEASE ASSOCIATED WITH SPLICING ABNORMALITIES

CROSS-CITE TO RELATED APPLICATIONS

The present application is a 37 C.F.R. § 1.53(b) divisional of U.S. application Ser. No. 16/486,980 filed Nov. 27, 2019, which is the national stage entry of PCT/JP2018/006070 filed Feb. 20, 2018, which claims priority on Japanese Patent Application No. 2017-029306 filed Feb. 20, 2017. The contents of each application is hereby incorporated by reference.

TECHNICAL FIELD

The present disclosure relates to a pharmaceutical composition for genetic diseases caused by aberrant splicing events, and a method for, using the pharmaceutical composition preventing, ameliorating, suppressing progression of, and/or treating genetic diseases caused by an aberrant splicing regulation.

BACKGROUND ART

Patent Document 1 discloses a reporter system capable of detecting alternative splicing, and a method for identifying a compound that affects alternative splicing, using the reporter system.

PRIOR ART DOCUMENTS

Patent Document

[Patent Document 1] WO 2011/152043 A1 (U.S. Pat. No. 9,273,364B2)

DISCLOSURE OF INVENTION

Problem to be Solved by the Invention

Various genetic diseases resulting from aberrant splicing are known. Fabry disease is known as one of such genetic diseases. Fabry disease is a disease, to which a genetic mutation in alternative splicing or the like resulting from a splicing mutation is attributed. In recent years, although enzyme replacement therapy by a recombinant a-galactosidase A (GLA) enzyme protein has been developed for Fabry disease, Fabry disease patients still rely on many symptomatic therapies. Thus, in general, development of curative therapeutics with a novel strategy has been unmet clinical needs for various genetic diseases caused by aberrant splicing events.

In one or more embodiments, the present disclosure provides a pharmaceutical composition capable of preventing, ameliorating, suppressing progression of, and/or treating genetic diseases caused by aberrant splicing events, and a method for, using the pharmaceutical composition, preventing, ameliorating, suppressing progression of, and/or treating genetic diseases caused by aberrant splicing events.

Means for Solving Problem

In one or more embodiments, the present disclosure relates to a pharmaceutical composition for preventing, ameliorating, suppressing progression of, and/or treating genetic diseases caused by aberrant splicing events, the pharmaceutical composition containing, as an active ingredient, a compound capable of suppressing an aberrant splicing that contributes to the development or progression of genetic diseases.

In one or more embodiments, the present disclosure relates to a method for preventing, ameliorating, suppressing progression of, and/or treating genetic diseases caused by aberrant splicing events, and the method includes administering a compound capable of suppressing a splicing abnormality that contributes to the development or progression of the genetic diseases to a subject that requires the compound.

In one or more embodiments, the present disclosure relates to a pharmaceutical composition for preventing, ameliorating, suppressing progression of, and/or treating Fabry disease, the pharmaceutical composition containing an active ingredient capable of suppressing a splicing abnormality that contributes to the development or progression of the Fabry disease.

In one or more embodiments, the present disclosure relates to a pharmaceutical composition for preventing, ameliorating, suppressing progression of, and/or treating Fabry disease, the pharmaceutical composition containing, as an active ingredient, a compound represented by Formula (I) or (I') below, a prodrug thereof, or a pharmaceutically acceptable salt thereof,

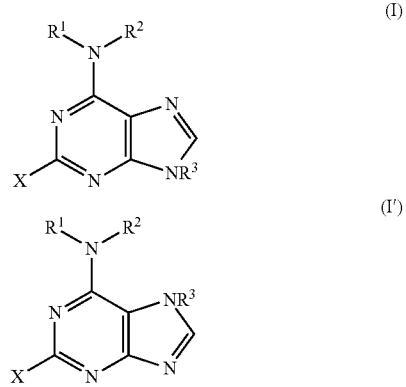

where, in Formulae (I) and (I'),
  $R^1$ and $R^2$ each independently represent a hydrogen atom, a linear, branched, or cyclic alkyl group having 1 to 6 carbon atoms, a benzyl or heteroarylmethyl group, a substituted or unsubstituted aryl group, or a substituted or unsubstituted heteroaryl group;
  $R^3$ represents a hydrogen atom, a linear, branched, or cyclic alkyl group having 1 to 6 carbon atoms, a benzyl or heteroarylmethyl group, a substituted or unsubstituted aryl group, a substituted or unsubstituted heteroaryl group, or $CH_2OC(O)R^4$—;
  $R^4$ represents a linear, branched, or cyclic alkyl group having 1 to 6 carbon atoms, a benzyl or heteroarylmethyl group, a substituted or unsubstituted aryl group, or a substituted or unsubstituted heteroaryl group; and
  X represents a hydrogen atom, a halogen atom, an amino group, an $R^1$- and $R^2$-substituted amino group, an azide group, a cyano group, a nitro group, a hydroxy group, a linear, branched, or cyclic alkyloxy group having 1 to 6 carbon atoms, a substituted or unsubstituted aryloxy group, a substituted or unsubstituted heteroaryloxy group, a mercapto group, a linear, branched, or cyclic alkylthio group having 1 to 6 carbon atoms, a substituted or unsubstituted arylthio group, a substituted or unsubstituted heteroarylthio group, a linear, branched, or cyclic alkyl group having 1 to 6 carbon atoms, a benzyl or heteroarylmethyl group, a substituted or unsubstituted aryl group, or a substituted or unsubstituted heteroaryl group.

In one or more embodiments, the present disclosure relates to a pharmaceutical composition for preventing, ameliorating, suppressing progression of, and/or treating Fabry disease, the pharmaceutical composition containing, as an active ingredient, a compound represented by Formula (IX) or (IX') below, a prodrug thereof, or a pharmaceutically acceptable salt thereof,

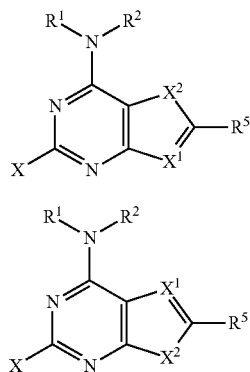

where, in Formulae (IX) and (IX'),
$R^1$ and $R^2$ each independently represent a hydrogen atom, a linear, branched, or cyclic alkyl group having 1 to 6 carbon atoms, a benzyl or heteroarylmethyl group, a substituted or unsubstituted aryl group, or a substituted or unsubstituted heteroaryl group;
$R^5$ represents a hydrogen atom, a halogen atom, a substituted or unsubstituted linear, branched, or cyclic alkoxy group having 1 to 6 carbon atoms;
$X^1$ represents N or CH;
$X^2$ represents —N($R^3$)—, S, or O;
$R^3$ represents a hydrogen atom, a $C_1$-$C_6$ alkyl group, a benzyl or heteroarylmethyl group, a substituted or unsubstituted aryl group, a substituted or unsubstituted heteroaryl group, or $CH_2OC(O)R^4$—;
$R^4$ represents a $C_1$-$C_6$ alkyl group, a benzyl or heteroarylmethyl group, a substituted or unsubstituted aryl group, or a substituted or unsubstituted heteroaryl group; and
X represents a hydrogen atom, a halogen atom, an amino group, an $R^1$- and $R^2$-substituted amino group, an azide group, a cyano group, a nitro group, a hydroxy group, a linear, branched, or cyclic alkyloxy group having 1 to 6 carbon atoms, a substituted or unsubstituted aryloxy group, a substituted or unsubstituted heteroaryloxy group, a mercapto group, a linear, branched, or cyclic alkylthio group having 1 to 6 carbon atoms, a substituted or unsubstituted arylthio group, a substituted or unsubstituted heteroarylthio group, a linear, branched, or cyclic alkyl group having 1 to 6 carbon atoms, a benzyl or heteroarylmethyl group, a substituted or unsubstituted aryl group, or a substituted or unsubstituted heteroaryl group.

In one or more embodiments, the present disclosure relates to a pharmaceutical composition for preventing, ameliorating, suppressing progression of, and/or treating Fabry disease, the pharmaceutical composition containing, as an active ingredient, a compound represented by Formula (X) or (X') below, a prodrug thereof, or a pharmaceutically acceptable salt thereof,

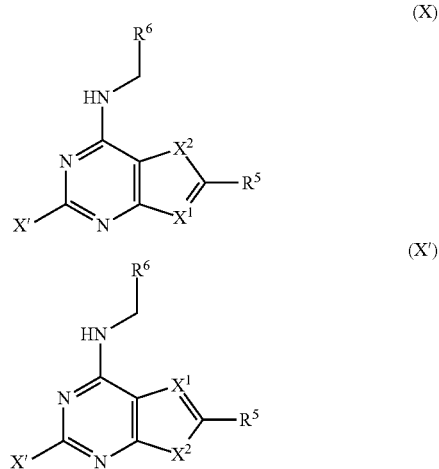

where, in Formulae (X) and (X'),
$R^5$ represents a hydrogen atom, a methoxy group, or a 2,2,2-trifluoroethoxy group;
$R^6$ represents a 2-furyl group, a 2-thiazolyl group, or a 4-pyridyl group;
$X^1$ represents N or CH;
$X^2$ represents NH, $NCH_3$, S, or O; and
X' represents a hydrogen atom, a chlorine atom, an iodine atom, a bromine atom, or a fluorine atom.

In one or more embodiments, the present disclosure relates to a method for preventing, ameliorating, suppressing progression of, and/or treating Fabry disease, and the method includes administering a pharmaceutical composition according to the present disclosure to a subject that requires the pharmaceutical compound.

BRIEF DESCRIPTION OF DRAWINGS

FIG. 3A shows one example in which, with regard to splicing of the normal GLA and the IVS4+919G>A mutant GLA, the fact that the production of a normal isoform (pseudo exon skipping) is restored through treatment with Compound 1 was confirmed by RT-PCR. The control, for which intracellular Glyceraldehyde 3-phosphate dehydrogenase (GAPDH) is used, is shown in a lower panel, showing that the amounts of RNA used in analysis are equal to each other. FIG. 3B is a schematic diagram, illustrating GLA splice switching and recovery of an active enzyme using Compound 1.

DESCRIPTION OF THE INVENTION

Figure 1:
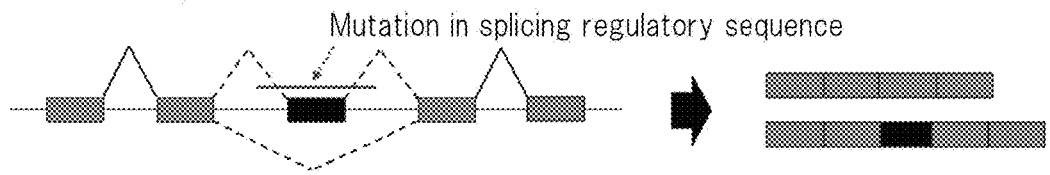
FIG. 1 is a conceptual diagram illustrating splicing mutations found in genetic diseases.
Figure 1:
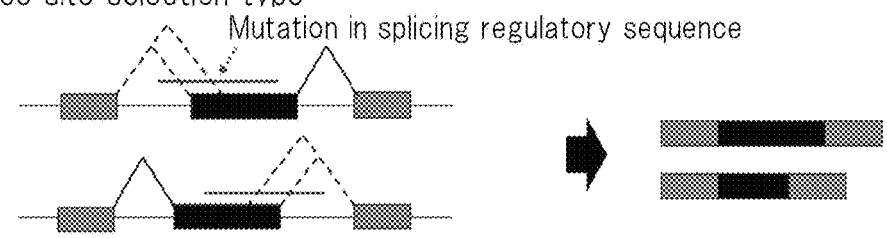
Figure 1:
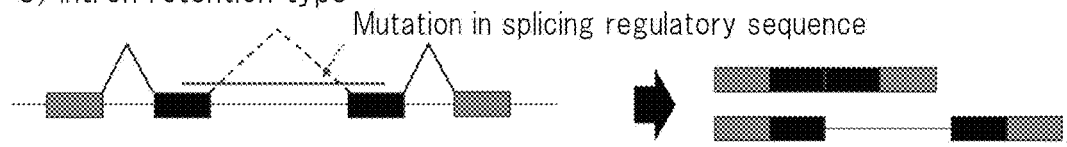
Figure 1:
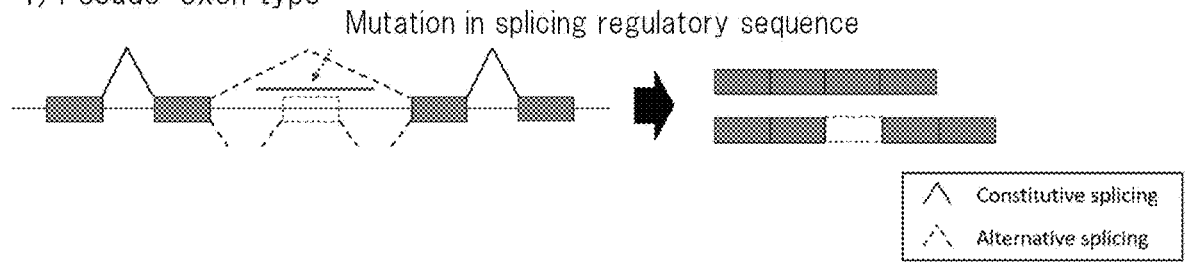

Various genetic diseases caused by an aberrant splicing regulation are known. Splicing mutations found in genetic diseases are classified into 1) an exon skipping type, 2) a splice site selection type, 3) an intron retention type, and 4) a pseudo exon type (FIG. 1).

An exon skipping mutation refers to a splicing mutation in which an exon that is normally recognized cannot be recognized (skipping occurs) due to a mutation within the exon or a peripheral intron sequence. An exon skipping mutation results in suppression or loss of a 5' splice site, suppression or loss of a 3' splice site, suppression or loss of an enhancer element, or formation of a silencer element. Out of exon skipping mutations, mutations other than mutations in GU located at the 5' splice site +1 or +2 and AG located at the 3' splice site −1 or −2, which are essential for splicing, are considered as targets for splicing therapeutic agents.

A splice site selection mutation refers to a splicing mutation in which a plurality of 5' splice sites or 3' splice sites occur due to a mutation in a splicing regulatory sequence in an exon region or an intron region. Similarly to exon skipping mutations, mutations other than mutations in GU located at the 5' splice site +1 or +2 and AG located at the 3' splice site −1 or −2, which are essential for splicing, are considered as targets for splicing therapeutic agents.

An intron-retention mutation refers to a splicing mutation in which recognition of an intron region (intron definition) is incomplete due to a mutation in an exon or intron region near the 5' splice site or the 3' splice site, and intron retention is induced. Similarly to exon skipping mutations, mutations other than mutations in GU located at the 5' splice site +1 or +2 and AG located at the 3' splice site −1 or −2, which are essential for splicing, are considered as targets for splicing therapeutic agents.

A pseudo exon mutation refers to a splicing mutation in which a sequence that is originally a sequence of an intron region is recognized as an exon due to a mutation. A pseudo exon mutation occurs due to a newly created 5' splice site, 3' splice site, or enhancer element, or suppression or loss of a silencer element occurring due to a mutation occurring within an intronic sequence. As for pseudo exon mutations, any pseudo exon mutations are considered as targets for splicing therapeutic agents.

Inventors of the present invention found a compound capable of enhancing exon recognition in splicing in which exon recognition is incomplete due to a splicing abnormality, and a compound capable of suppressing exon recognition in the splicing. Also, the inventors found that a compound capable of enhancing exon recognition in splicing in which exon recognition is incomplete due to a splicing abnormality exhibits therapeutic effects on both exon skipping mutations and pseudo exon mutations. Also, the inventors found that a compound capable of suppressing exon recognition in splicing in which exon recognition is incomplete due to a splicing abnormality exhibits therapeutic effects on pseudo exon mutations. The inventors found that a compound capable of suppressing exon recognition in splicing in which exon recognition is incomplete due to a splicing abnormality exhibits the effects of inducing a functional splicing isoform in an exon (a PTC exon) into which a premature termination codon (PTC) is introduced, and being capable of avoiding PTC.

Examples of genetic diseases caused by an aberrant splicing regulation resulting from exon skipping mutations include Pompe disease, mucopolysaccharidoses, congenital long QT syndrome, Fukuyama congenital muscular dystrophy, progeria syndrome, amyotrophic lateral sclerosis, atypical adenofibrosis, autism, autism spectrum disorder, Charcot-Marie-Tooth disease, CHARGE syndrome, dementia, epilepsy, epileptic encephalopathies, familial dysautonomia (IKBKAP), familial isolated growth hormone deficiency type II, Frasier syndrome, frontotemporal dementia, Parkinson's disease, Huntington's disease, Marfan syndrome, mental retardation, Menkes disease, muscular dystrophy, myopathy, myotonic dystrophy type I, myotonic dystrophy type 2, neurofibromatosis type 1, von Recklinghausen NF, peripheral NF, occipital horn syndrome, retinoblastoma, schizophrenia, and tuberous sclerosis.

Examples of genetic diseases caused by an aberrant splicing regulation resulting from pseudo exon mutations include Fabry disease (GLA), cystic fibrosis (CFTR), homocystinuria (MTRR), hereditary breast/ovarian cancer syndrome (BRCA 1, BRCA 2), ataxia-telangiectasia/Louis-Bar syndrome (ATM), Lynch syndrome (MSH2), neurofibromatosis type 1 (NF1), tuberous sclerosis (TSC2), atypical pyridoxine-dependent epilepsy (ALDH7A1), Leber congenital amaurosis (CEP290), Alport syndrome (COL4A3), chronic granulomatous disease (CYBB), 17a-hydroxylase deficiency (CYP17A1), Marfan syndrome (FBN1), X-linked hypophosphatemia (PHEX), and polycystic kidney disease (PKHD1) (responsible genes with pseudo exon are indicated in parentheses).

Examples of genetic diseases in which it is expected that a PTC can be avoided in a similar manner through induction of a splicing isoform include Alport syndrome (COL4A5), Bartter syndrome (CLCNKA), Becker muscular dystrophy (DMD), hereditary ovarian cancer and breast cancer (BRCA1, BRCA2, PALB2), colon cancer/T-cell acute lymphoblastic leukemia (BAX), arrhythmia (KCNH2), cardiomyopathy (TNNT2), Carney complex (PRKAR1A), CHARGE syndrome (CHD7), chronic granulomatous disease (CYBB), ciliary dyskinesia syndrome (ZMY7ND10), Cockayne syndrome (ERCC8), congenital disorders of glycosylation type I (SSR4), Cornelia de Lange syndrome (NIPBL), cystic fibrosis (CFTR), hearing impairment (RDX, OTOF, SMPX), dilated cardiomyopathy (DSP), Duchenne muscular dystrophy (TTN, DMD), familial adenomatous polyposis (APC), hypertrophic cardiomyopathy (MYBPC3), fibrochondrogenesis (COL11A1), Finnish congenital nephrotic syndrome (NPHS1), P-galactosidase deficiency (GALC), glycogen storage disease type III (AGL), hereditary neoplastic syndrome (CDH1, STK11), Hermansky-Pudlak syndrome (HPS5), hypogonadotropic hypogonadism (TACR3), I-cell disease (GNPTAB), juvenile polyposis syndrome (SMAD4), limb-girdle muscular dystrophy (CAPN3, ANO5), lissencephaly (PAFAH1B1), Lynch syndrome (MLH1, PMS2), Marfan syndrome (FBN1), meconium ileus (GUCY2C), merosin-deficient muscular dystrophy (LAMA2), congenital mirror movement disorder (DCC), Miyoshi muscular dystrophy, mucolipidosis type III (GNPTG), myopathy, early-onset-areflexia-respiratory-distress-dysphagia (MEGF10), nemaline myopathy, nonimmunologic hydrops fetalis (NEB), neutral lipid storage disease with myopathy (PNPLA2), nonketotic hyperglycinemia (GLDC), Hurler syndrome (IDUA), maple syrup urine disease (BCKDHA), oligodontia-colorectal cancer syndrome (AXIN2), orofaciodigital syndrome (OFD1), gyrate atrophy (OAT), Nance-Sweeney syndrome (COL11A2), palmoplantar keratoderma (SERPINB7), Parkinson's disease (LRRK2), phenylketonuria (PAH), pituitary hormone deficiency (POU1F1), pyridoxine-dependent epilepsy (ALDH7AI), severe combined immunodeficiency (JAK3), severe myoclonic epilepsy of infancy (SCN1A), myotubular myopathy (MTM), Sotos syndrome (NSD1), spinal muscular atrophy (SMN1), spinocerebellar ataxia (ANO10), tuberous sclerosis (TSC2), and familial tumoral calcinosis (GALNT3)(responsible genes with PTC are indicated in parentheses).

Pharmaceutical Composition for Genetic Diseases Resulting from an Aberrant Splicing Regulation In one or more embodiments, the present disclosure relates to a pharmaceutical composition for preventing, ameliorating, suppressing progression of, and/or treating genetic diseases caused by an aberrant splicing regulation, the pharmaceutical composition containing, as an active ingredient, a compound capable of suppressing a splicing abnormality that contributes to the development or progression of the genetic diseases. In one or more embodiments, the pharmaceutical composition of the present disclosure contains, as an active ingredient, a compound capable of enhancing exon recognition in splicing in which exon recognition is incomplete due to a splicing mutation, and a compound capable of suppressing recognition of an exon created by a splicing mutation.

In one or more embodiments, examples of the compound capable of enhancing exon recognition in splicing in which exon recognition is incomplete due to a splicing mutation include compounds represented by Formulae (II), (II'), and (III). In one or more embodiments, examples of the compound capable of suppressing exon recognition in the splicing include compounds represented by Formulae (IV), (V), (VI), (VII), and (VIII).

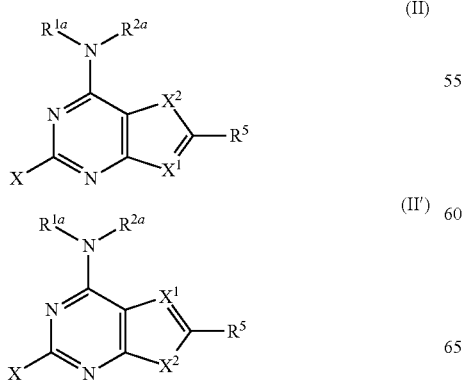

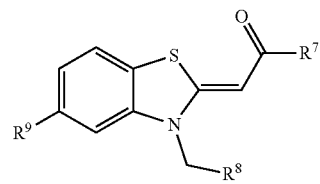

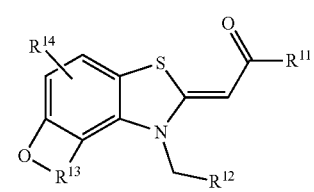

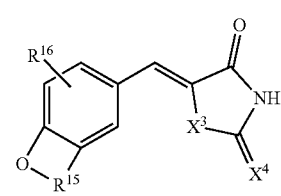

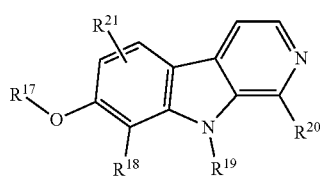

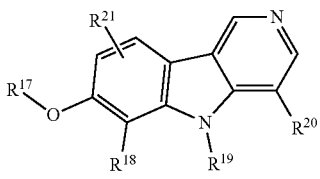

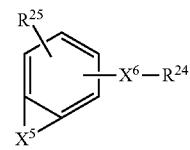

In Formulae (II) and (II'), $R^{1a}$ and $R^{2a}$ each independently represent a hydrogen atom, a substituted or unsubstituted $C_{1-6}$ alkyl group, a substituted or unsubstituted benzyl group, a substituted or unsubstituted heteroarylmethyl group, a substituted or unsubstituted heteroarylethyl group, a substituted or unsubstituted aryloxy group, a substituted or unsubstituted heteroaryloxy group, a substituted or unsubstituted alkoxyamidoalkyl group, a substituted or unsubstituted aryl group, or a substituted or unsubstituted heteroaryl group, or alternatively $R^{1a}$ and $R^{2a}$ bind to each other to form a ring together with N, and the ring is a substituted or unsubstituted monocyclic heterocyclic ring, or a substituted or unsubstituted bicyclic heterocyclic ring;

$R^5$ represents a hydrogen atom, a halogen atom, or a substituted or unsubstituted $C_1$-$C_6$ alkoxy group;

$X^1$ represents N or CH;

$X^2$ represents —N($R^3$)—, S, or O;

$R^3$ represents a hydrogen atom, a $C_1$-$C_6$ alkyl group, a benzyl or heteroarylmethyl group, a substituted or unsubstituted aryl group, a substituted or unsubstituted heteroaryl group, or CH$_2$OC(O)R$^4$—;

R$^4$ represents a C$_1$-C$_6$ alkyl group, a benzyl or heteroarylmethyl group, a substituted or unsubstituted aryl group, or a substituted or unsubstituted heteroaryl group; and X represents a hydrogen atom, a halogen atom, an amino group, an R$^{1a}$- and R$^{2a}$-substituted amino group, an azido group, a cyano group, a nitro group, a hydroxy group, a C$_1$-C$_6$ alkyl group, a substituted or unsubstituted aryloxy group, a substituted or unsubstituted heteroaryloxy group, a mercapto group, a linear, branched, or cyclic alkylthio group having 1 to 6 carbon atoms, a substituted or unsubstituted arylthio group, a substituted or unsubstituted heteroarylthio group, a benzyl or heteroarylmethyl group, a substituted or unsubstituted aryl group, or a substituted or unsubstituted heteroaryl group.

In Formula (II) or (II'), if X$^1$ and X$^2$ respectively represent N and NH, Formulae (II) and (II') above are tautomers. Although only one tautomer is illustrated in the above-described specific examples, disclosure of one tautomer also discloses the other tautomer in the present disclosure. If a compound represented by Formula (II) or (II') includes an asymmetric carbon atom, and/or if a stereoisomer thereof is present, the compound may be a mixture of isomers or an isolated isomer, in one or more embodiments.

In Formula (III),

R$^7$ and R$^8$ each independently represent a hydrogen atom, a halogen-substituted or unsubstituted C$_1$-C$_{10}$ alkyl group, or a C$_2$-C$_6$ alkenyl group;

R$^9$ represents a hydrogen atom, a halogen atom, or a halogen-substituted or unsubstituted C$_1$-C$_{10}$ alkyl group, —OR$^{10}$, —NHR$^{10}$, or —N(R$^{10}$)$_2$; and R$^{10}$ represents a hydrogen atom or a C$_1$-C$_{10}$ alkyl group.

In Formula (IV),

R$^{11}$ and R$^{12}$ each independently represent a hydrogen atom or a C$_1$-C$_6$ alkyl group;

R$^{13}$ represents

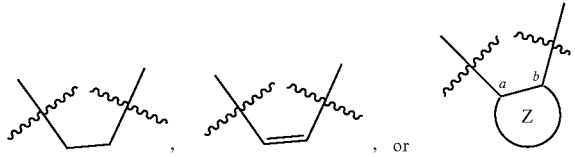

, or where Z forms, together with atoms marked with a and b, a ring selected from the group consisting of one benzene ring, one heteroaromatic ring, an aromatic ring fused with one or more benzene rings, a heteroaromatic ring fused with one or more heteroaromatic rings, a mixed fused polycyclic ring in which one or more benzene rings and one or more heteroaromatic rings are fused, and cycloaliphatic compounds, and the ring may include one or more substituents, the substituents being a hydrogen atom, a halogen atom, or a C$_1$-C$_6$ alkyl group, and an atonic bonding to which a wavy line is attached indicates a portion that binds to Formula (IV); and R$^{14}$ represents a hydrogen atom, a halogen atom, or a C$_1$-C$_6$ alkyl group.

In Formula (V),

X$^3$ and X$^4$ each independently represent S or NH,

R$^{15}$ represents

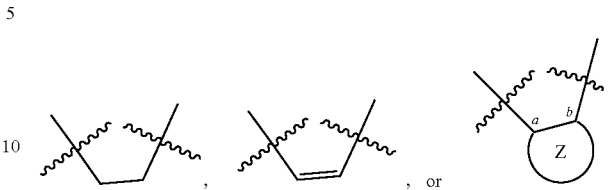

, or where Z forms, together with atoms marked with a and b, a ring selected from the group consisting of one benzene ring, one heteroaromatic ring, an aromatic ring fused with one or more benzene rings, a heteroaromatic ring fused with one or more heteroaromatic rings, a mixed fused polycyclic ring in which one or more benzene rings and one or more heteroaromatic rings are fused, and cycloaliphatic compounds, and the ring may include one or more substituents, the substituents being a hydrogen atom, a halogen atom, or a C$_1$-C$_6$ alkyl group, and an atomic bonding to which a wavy line is attached indicates a portion that binds to Formula (V); and R$^{16}$ represents a hydrogen atom, a halogen atom, or a C$_1$-C$_6$ alkyl group;

In Formulae (VI) and (VII),

R$^{17}$ and R$^{19}$ each independently represent a hydrogen atom, a C$_1$-C$_6$ alkyl group, a benzyl or heteroarylmethyl group, a substituted or unsubstituted aryl group, or a substituted or unsubstituted heteroaryl group;

R$^{18}$ represents —R$^{22}$, —C≡C—R$^{22}$, —CH=CH—R$^{22}$, or —O—(CH$_2$)n-R$^{22}$, n is 1 to 6, R$^{22}$ represents a hydrogen atom, a hydroxy group, a C$_1$-C$_8$ alkyl group, —Si(R$^{23}$)$_3$, a substituted or unsubstituted phenyl group, a monocyclic heteroaromatic group, or a cycloaliphatic group, or alternatively, R$^{17}$ and R$^{18}$ bind to each other to form a ring, and —R$^{17}$-R$^{18}$ is substituted by —(CH$_2$)m-CH$_2$—, —CH=CH—, —(CH$_2$)m-O—, or a halogen atom, m is 1 to 6, R$^{23}$ represents a hydrogen atom, a C$_1$-C$_6$ alkyl group, a trihalo-methyl group, or a hydroxy group, and three R$^{23}$ of —Si(R$^{23}$)$_3$ may be different from each other; and R$^{20}$ and R$^{21}$ each represent a hydrogen atom or a C$_1$-C$_6$ alkyl group.

In Formula (VIII),

X$^5$ represents or where R$^{26}$, R$^{27}$, and R$^{28}$ each independently represent a hydrogen atom, a halogen atom, a carboxyl group, an amino group, a hydroxy group, a C$_1$-C$_4$ alkyl group, or a halogen-substituted C$_1$-C$_4$ alkyl group, and an atomic bonding to which a wavy line is attached indicates a portion that binds to Formula (VIII);

X$^6$ represents -(atomic bonding) or —NH—;

R$^{24}$ represents

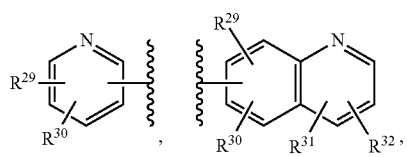

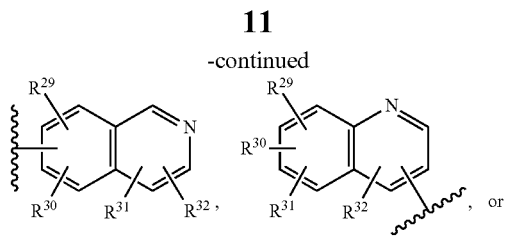

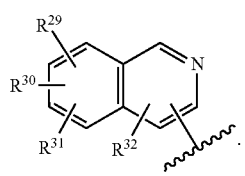

where $R^{29}$, $R^{30}$, $R^{31}$, and $R^{32}$ each independently represent a hydrogen atom, a halogen atom, a carboxyl group, an amino group, a hydroxy group, a $C_1$-$C_4$ alkyl group, or a halogen-substituted $C_1$-$C_4$ alkyl group, and an atomic bonding to which a wavy line is attached indicates a portion that binds to Formula (VIII); and $R^{25}$ represents a hydrogen atom, a halogen atom, a carboxyl group, an amino group, a hydroxy group, a halogen-substituted or unsubstituted $C_1$-$C_4$ alkyl group.

In the present disclosure, the number of substituents of a "substituted or unsubstituted group" may be one or more and the substituents may be the same as or different from each other, and in one or more embodiments, examples thereof include a halogen atom, a cyano group, a trifluoromethyl group, a nitro group, a hydroxy group, a methylenedioxy group, a lower alkyl group, a lower alkoxy group, a benzyloxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanoylamino group, and a lower alkylsulfonamide group. In one or more embodiments, examples of the halogen atom include a fluorine atom, a chlorine atom, a bromine atom, and an iodine atom.

In one or more embodiments, examples of the compound represented by Formula (II) or (II') include the compounds below.

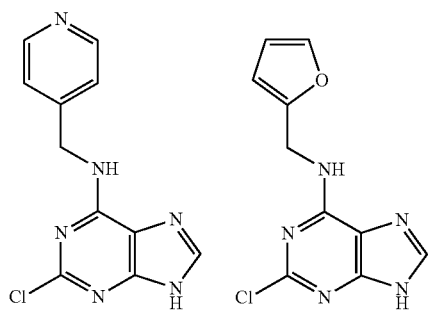

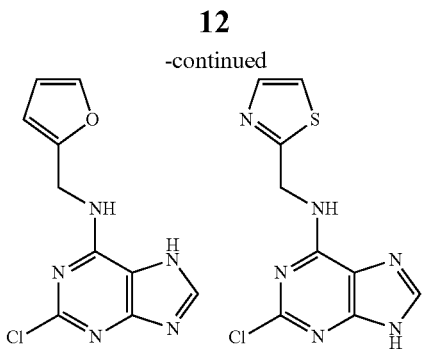

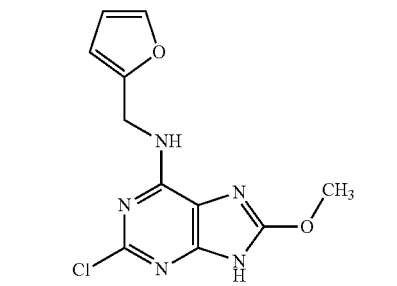

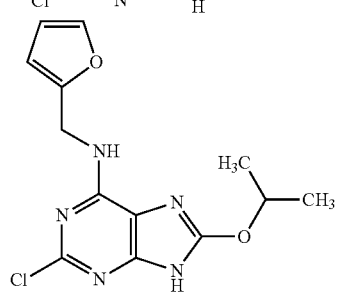

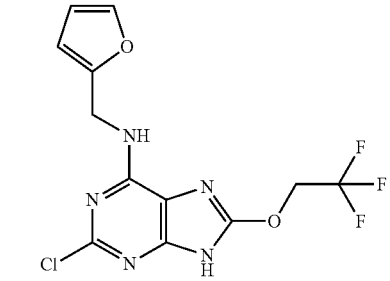

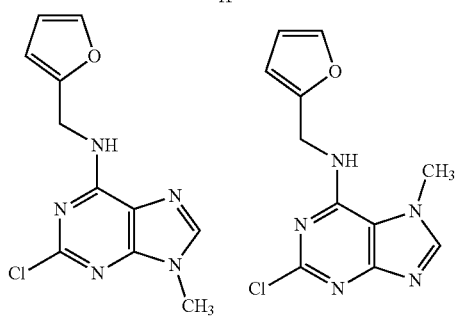

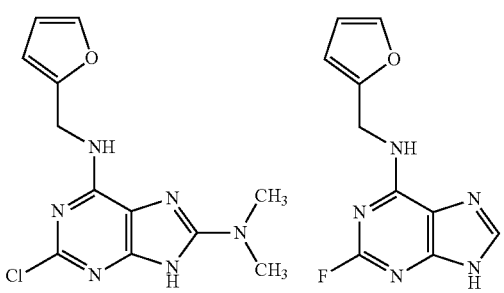

-continued

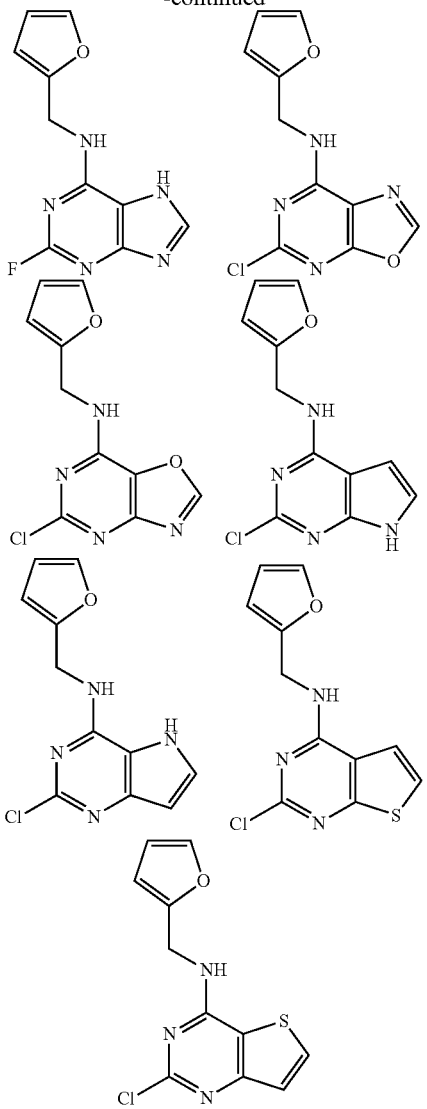

In one or more embodiments of the compound represented by Formula (III), $R^7$ and $R^8$ each independently represent a hydrogen atom, a methyl group, a halogen-substituted methyl group, a trifluoromethyl group, an ethyl group, a halogen-substituted ethyl group, and a trifluoroethyl group, and $R^9$ represents a hydrogen atom, a halogen atom, a methyl group, a trifluoromethyl group, an ethyl group, a trifluoroethyl group, —$OR^{10}$, —$NHR^{10}$, or —$N(R^{10})_2$, and $R^{10}$ represents a hydrogen atom, a methyl group, or an ethyl group.

In one or more embodiments, examples of the compound represented by Formula (III) include the compounds below,

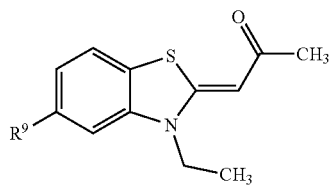

-continued

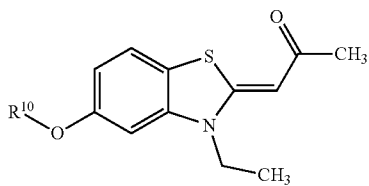

where, in the formula, $R^9$ represents a hydrogen atom, a halogen atom, or a halogen-substituted or unsubstituted $C_1$-$C_{10}$ alkyl group, and preferably a hydrogen atom, a fluorine atom, a chlorine atom, a methyl group, or an ethyl group, and $R^{10}$ represents a hydrogen atom or a $C_1$-$C_{10}$ alkyl group, and preferably a hydrogen atom, a methyl group, or an ethyl group.

In one or more embodiments, examples of the compound represented by Formula (III) include the compounds below.

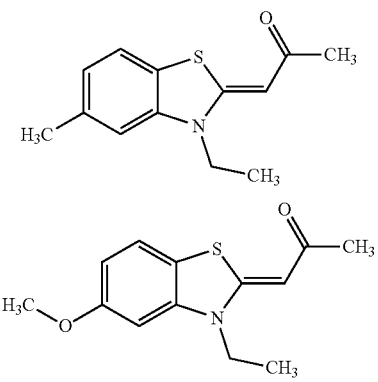

In one or more embodiments, examples of the compound represented by Formula (IV) include the compounds below,

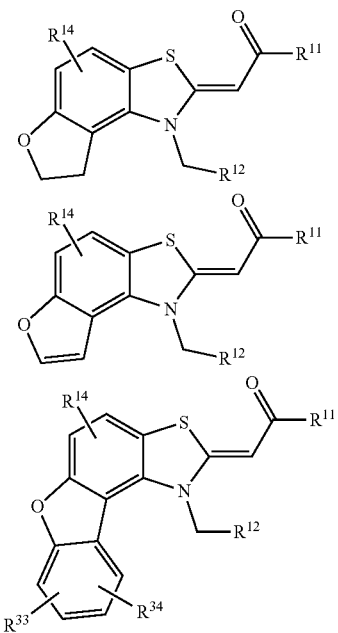

-continued

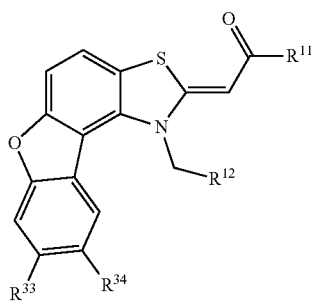

where, in the formula, $R^{11}$ and $R^{12}$ each independently represent a hydrogen atom or a $C_1$-$C_6$ alkyl group, and preferably a hydrogen atom, a methyl group, or an ethyl group, and more preferably a methyl group, $R^{14}$ represents a hydrogen atom, a halogen atom, or a $C_1$-$C_6$ alkyl group, and preferably a hydrogen atom, a fluorine atom, a chlorine atom, or a methyl group, and $R^{33}$ and $R^{34}$ each independently represent a hydrogen atom, a halogen atom, or a $C_1$-$C_6$ alkyl group, and preferably a hydrogen atom, a fluorine atom, a chlorine atom, or a methyl group, and more preferably, one of $R^{33}$ and $R^{34}$ represents a hydrogen atom and the other represents a chlorine atom or a methyl group, or both represent a methyl group.

In one or more embodiments, examples of the compound represented by Formula (IV) include the compounds below,

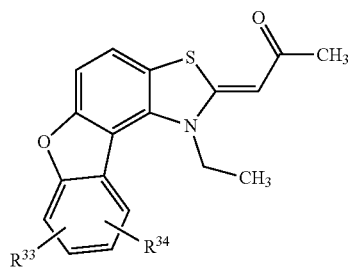

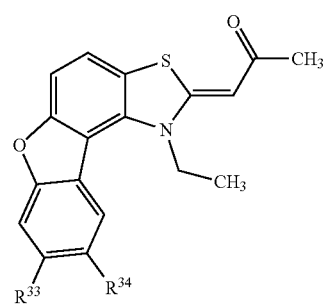

where, in the formula, $R^{33}$ and $R^{34}$ each independently represent a hydrogen atom, a halogen atom, or a $C_1$-$C_6$ alkyl group, and preferably a hydrogen atom, a fluorine atom, a chlorine atom, or a methyl group, and more preferably, one of $R^{33}$ and $R^{34}$ represents a hydrogen atom and the other represents a chlorine atom or a methyl group, or both represent a methyl group.

In one or more embodiments, examples of the compound represented by Formula (IV) include the compounds below.

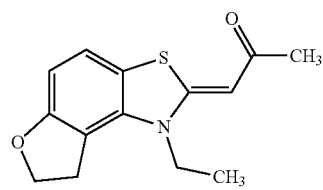

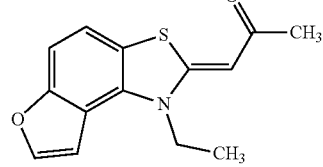

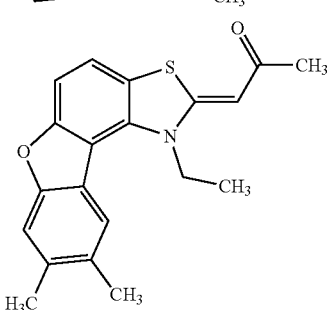

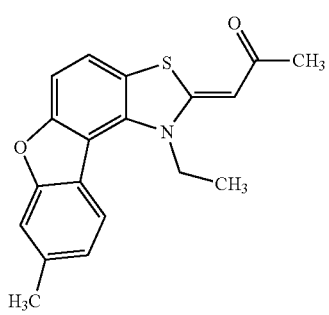

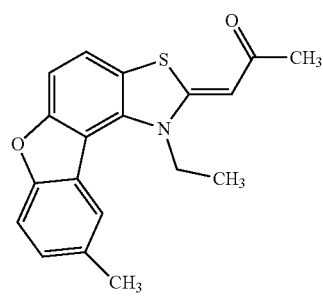

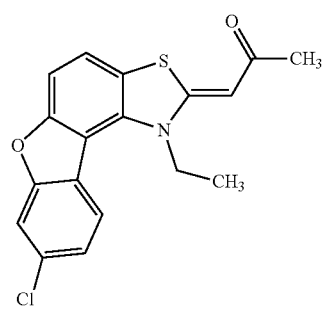

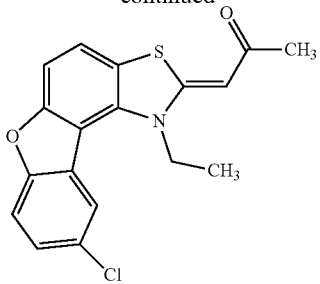

In one or more embodiments, examples of the compound represented by Formula (V) include the compounds below,

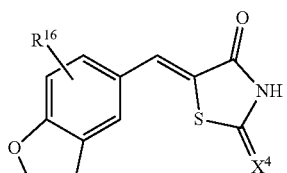

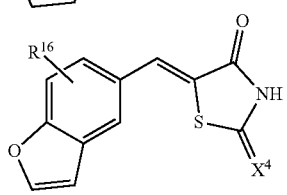

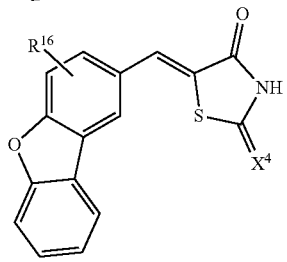

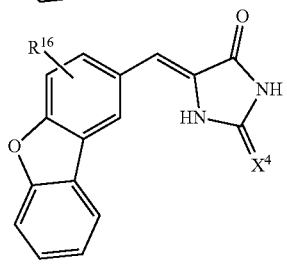

where, in the formula, $R^{16}$ represents a hydrogen atom, a halogen atom, or a $C_1$-$C_6$ alkyl group, and preferably a hydrogen atom, and $X^4$ represents S or NH.

In one or more embodiments, examples of the compound represented by Formula (VI) or (VII) include the compounds below,

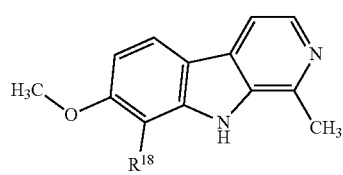

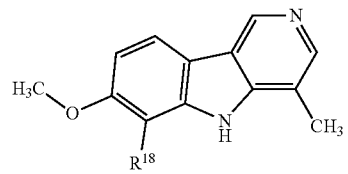

where $R^{18}$ represents a hydrogen atom, a hydroxy group, or a $C_1$-$C_6$ alkyl group, and preferably a hydrogen atom, a hydroxy group, or a methyl group.

In one or more embodiments, examples of the compound represented by Formula (VI) or (VII) include the compounds below.

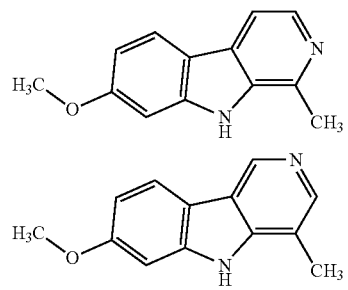

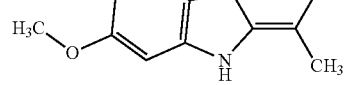

In one or more embodiments, examples of the compound represented by Formula (VIII) include the compounds below,

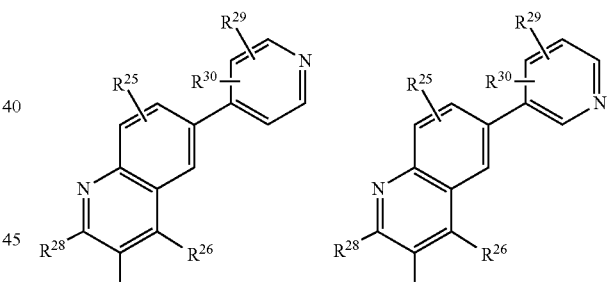

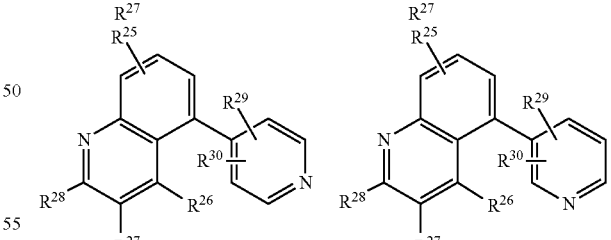

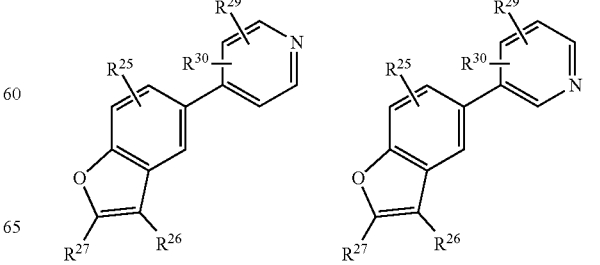

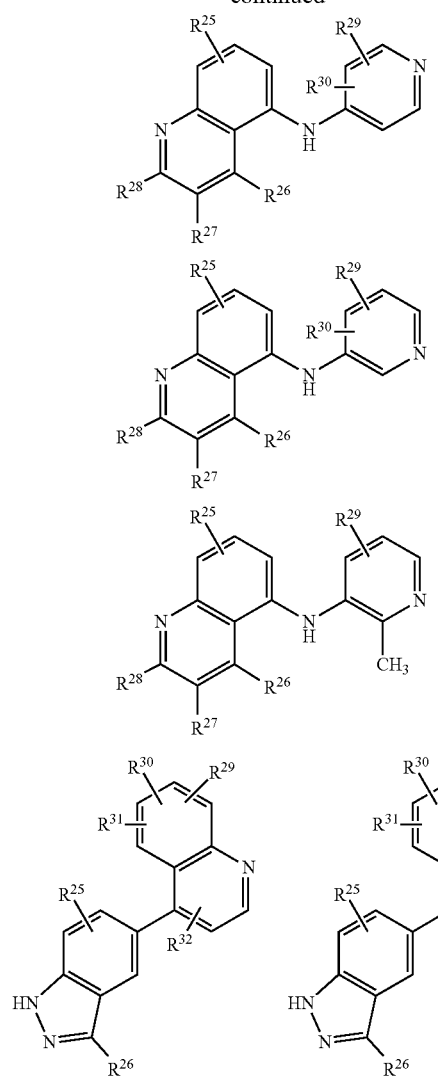

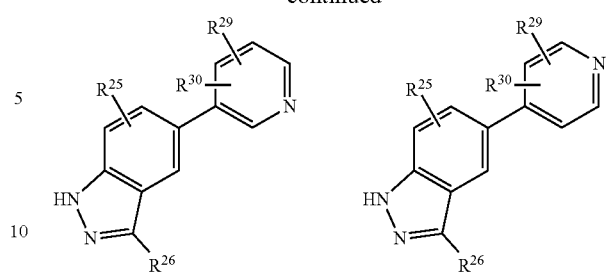

where, in the formula, $R^{25}$, $R^{26}$, $R^{27}$, $R^{28}$, $R^{29}$, $R^{30}$, $R^{31}$, and $R^{32}$ each independently represent a hydrogen atom, a halogen atom, a carboxyl group, an amino group, a hydroxy group, a $C_1$-$C_4$ alkyl group, or a halogen-substituted $C_1$-$C_4$ alkyl group, and preferably a hydrogen atom, a fluorine atom, a chlorine atom, or a methyl group.

In one or more embodiments, examples of the compound represented by Formula (VIII) include the compounds below.

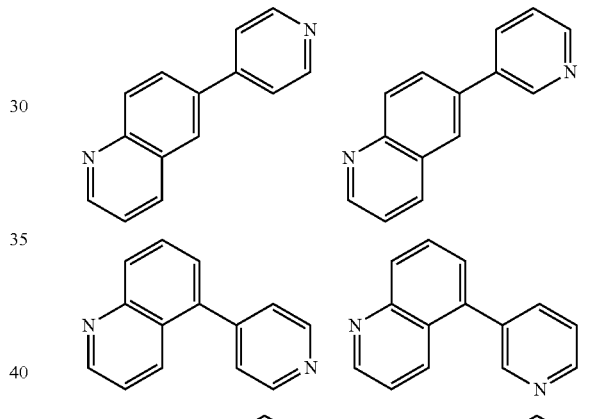

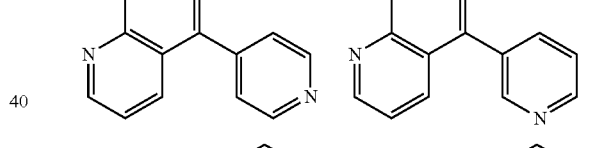

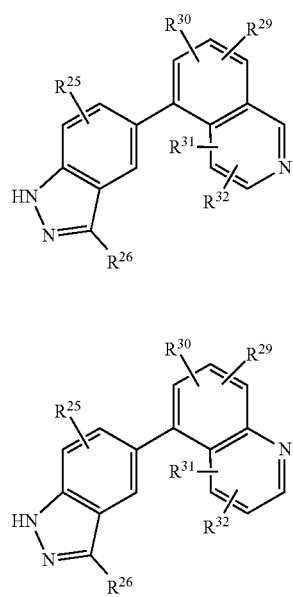

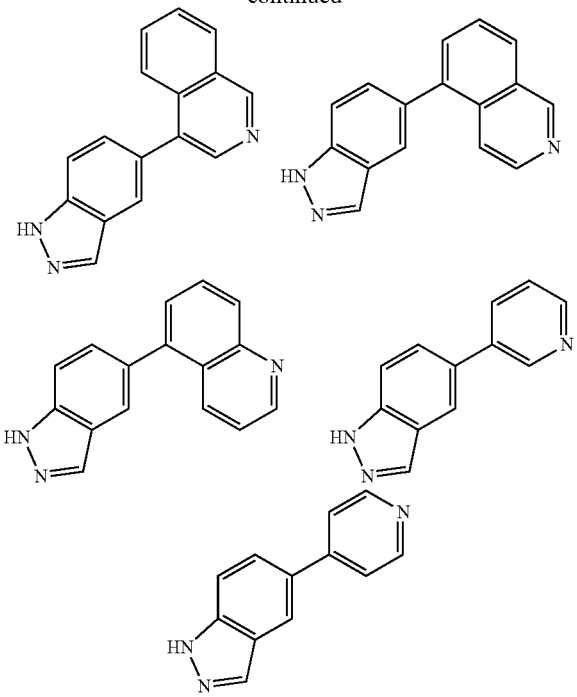

In one or more embodiments, the pharmaceutical composition according to the present disclosure contains, as an active ingredient, a compound represented by Formula (II), (II'), (III), (IV), (V), (VI), (VII), or (VIII), or a combination thereof, and may further contain a medicinally acceptable carrier, an antiseptic, a diluent, an excipient, or other medicinally acceptable component.

Method for Preventing, Ameliorating, Suppressing Progression of, and/or Treating Genetic Diseases Resulting from an Aberrant Splicing Regulation As another aspect, the present disclosure relates to a method for preventing, ameliorating, suppressing progression of, and/or treating genetic diseases caused by aberrant splicing events, and the method includes administering a compound capable of suppressing a splicing abnormality that contributes to the development or progression of the genetic diseases to a subject that requires the compound. In one or more embodiments, examples of the compound include compounds capable of enhancing exon recognition in splicing in which exon recognition is incomplete due to a splicing abnormality or compounds capable of suppressing exon recognition, and specific examples thereof, which are not particularly limited, include compounds represented by Formula (II), (II'), (III), (IV), (V), (VI), (VII), or (VIII).

Fabry disease is a genetic disease resulting from an aberrant splicing regulation. Fabry disease is a disease, in which glycolipids such as globotriaosylceramide (Gb3) accumulate in lysosomes due to a deficiency of the GLA enzyme, which is a lysosomal hydrolase, resulting in various symptoms relating to various organs such as circulatory organs (e.g. the heart) and kidney.

Fabry disease is classified into three types according to symptoms: classic, atypical, and heterozygous. With classic Fabry disease, normally, the GLA enzyme activity is low or barely detectable. On the other hand, with atypical Fabry disease, especially with a cardiac variant (cardiac Fabry disease), whose symptoms mainly appear in the cardiovascular system, the GLA enzyme activity can be detectable, and thus, the onset age of atypical Fabry disease is higher than in classic Fabry disease. Although heterozygous Fabry diseases have individual differences, such as due to effects of X-chromosome inactivation in female, the symptoms of Fabry disease are often recognized.

Fabry disease screening of cardiac hypertrophy patients was performed, and it was reported that 3.0% of Japanese male patients with left ventricular hypertrophy (Nakao S et al., NEJM 333, 288-293, 1995), 6.3% of British patients diagnosed with hypertrophic cardiomyopathy after age 40 (Sachdev B et al., Circulation 105, 1407-1411, 2002), and 12% of Italian female patients with hypertrophic cardiomyopathy (Chimenti C et al., Circulation 110, 1047-1053, 2004) were Fabry disease. Thus, it has been pointed out that there is a possibility that patients with cryptogenic left ventricular hypertrophy and hypertrophic cardiomyopathy are likely to be cardiac Fabry disease patients.

A single base substitution (VS4+919G>A mutation) within the intron 4 of the GLA gene has been reported as etiology of a subset of cardiac Fabry disease patients. The IVS4+919G>A mutation results in alternative splicing in transcription of the GLA gene, and as a result, a GLA enzyme deficiency in lysosomes occurs. It has been reported that many cardiovascular abnormalities and the like are confirmed in adult Taiwanese people having the IVS4+919G>A mutation. Also, it has been reported that, when screening of Taiwanese newborns for the GLA enzyme activity was performed, about 70% to 80% of newborns with low plasma GLA enzyme activity and a causative mutation for Fabry disease had the IVS4+919G>A mutation (Lin H-Y, et al., Circ Cardiovasc Genet 2(5) 450-456 2009, Hwu W-L et al., Hum Mutat 30(10) 1397-1405 2009).

Pharmaceutical Composition for Fabry Disease

In one or more embodiments, the present disclosure relates to a pharmaceutical composition for preventing, ameliorating, suppressing progression of, and/or treating Fabry disease, the pharmaceutical composition containing an active ingredient capable of suppressing an aberrant splicing regulation that contributes to the development or progression of the Fabry disease (abnormal splicing that contributes to Fabry disease). In one or more embodiments, the pharmaceutical composition according to the present disclosure may be used to suppress an aberrant splicing regulation that contributes to Fabry disease.

In one or more embodiments, "An aberrant splicing regulation that contributes to Fabry disease" in the present disclosure results from a mutation in a gene to be spliced. In one or more non-limiting embodiments, an example of abnormal splicing that contributes to Fabry disease is splicing of a pre-mRNA of the mutant GLA gene having the IVS4+919G>A mutation (see the above description). In one or more embodiments, the pharmaceutical composition according to the present disclosure may be used to prevent, ameliorate, suppress progression of, and/or treat cardiac Fabry disease out of the Fabry diseases.

In one or more embodiments, the pharmaceutical composition according to the present disclosure may be used to alter abnormal splicing that contributes to Fabry disease in mammalian cells or mammalian individuals. In one or more embodiments, the abnormal splicing that contributes to Fabry disease may result from a mutation within a gene to be spliced. In another one or more embodiments, the abnormal splicing that contributes to Fabry disease may be splicing of a pre-mRNA of the mutant GLA gene with the IVS4+919G>A mutation.

In one or more embodiments, the pharmaceutical composition according to the present disclosure may be used to increase the ratio of normal splicing to abnormal splicing that contributes to Fabry disease in mammalian cells or mammalian individuals. In one or more embodiments, the abnormal splicing that contributes to Fabry disease may result from a mutation in a gene to be spliced. In another one or more embodiments, the abnormal splicing that contributes to Fabry disease may be splicing of a pre-mRNA of the mutant GLA gene having the IVS4+919G>A mutation.

In one or more embodiments, the pharmaceutical composition according to the present disclosure may be used to alter splicing of a pre-mRNA of the mutant GLA gene having the IVS4+919G>A mutation in human cells or human individuals. Also, in one or more embodiments, the pharmaceutical composition according to the present disclosure may be used to increase the ratio of normal splicing to splicing abnormality of a pre-mRNA of the mutant GLA gene having the IVS4+919G>A mutation in human cells or human individuals.

In one or more embodiments, mammalian cells or human cells of the present disclosure include in vivo cells, in vitro cells, or ex vivo cells. Also, in one or more embodiments, mammalian cells may be human cells or cells of a mammal other than a human.

In one or more embodiments, human cells and human individuals of the above-described embodiment may have the IVS4+919G>A mutation in the endogenous GLA gene. As described above, the IVS4+919G>A mutation of the present disclosure is a single base substitution (G→A) in intron 4 of the GLA gene. In one or more non-limiting embodiments, whether human cells and human individuals have an IVS4+919G>A mutation may be determined using a method for detecting a single base substitution. Alternatively, base sequence, array, and various gene amplification methods may be used.

In one aspect, the present disclosure relates to a pharmaceutical composition for preventing, ameliorating, suppressing progression of, and/or treating Fabry disease, the pharmaceutical composition containing, as an active ingredient, a compound represented by Formula (I) or (I'), a prodrug thereof, or a pharmaceutically acceptable salt thereof.

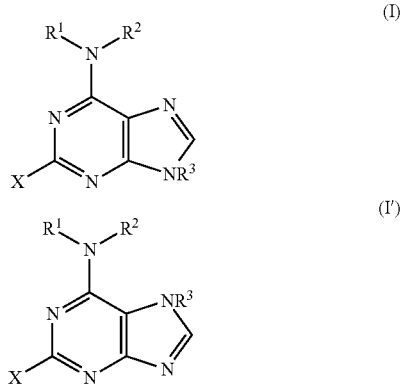

In Formulae (I) and (I'), $R^1$ and $R^2$ each independently represent a hydrogen atom, a linear, branched, or cyclic alkyl group having 1 to 6 carbon atoms, a benzyl or heteroarylmethyl group, a substituted or unsubstituted aryl group, or a substituted or unsubstituted heteroaryl group.

In one or more embodiments, examples of the linear or branched alkyl group having 1 to 6 carbon atoms represented by $R^1$ and $R^2$ include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group. Also, in one or more embodiments, examples of the cyclic alkyl group having 1 to 6 carbon atoms represented by $R^1$ and $R^2$ include cyclopropyl, cyclobutyl, cyclopentyl, and cyclohexyl.

In one or more embodiments, examples of the heteroaryl (including heteroaryl of the heteroarylmethyl group) represented by $R^1$ and $R^2$ include a 5- to 6-membered monocyclic group having 1 to 2 nitrogen atoms, a 5- to 6-membered monocyclic group having 1 to 2 nitrogen atoms and either 1 oxygen atom or 1 sulfur atom, a 5-membered monocyclic group having 1 oxygen atom or 1 sulfur atom, and a bicyclic group that has 1 to 4 nitrogen atoms and is formed through fusion of a 6-membered ring and a 5- or 6-membered ring. Also, in another one or more embodiments, examples of the heteroaryl include 2-pyridyl, 3-pyridyl, 4-pyridyl, 2-thienyl, 3-thienyl, 3-oxadiazolyl, 2-imidazolyl, 2-thiazolyl, 3-isothiazolyl, 2-oxazolyl, 3-isoxazolyl, 2-furyl, 3-furyl, 3-pyrrolyl, 2-quinolyl, 8-quinolyl, 2-quinazolinyl, and 8-purinyl. Examples of the aryl group represented by $R^1$ and $R^2$ include an aryl group having 10 or less carbon atoms, such as a phenyl group or a naphthyl group.

In one or more embodiments, the number of substituents of the aryl group and the heteroaryl group represented by $R^1$ and $R^2$ may be one or more, and the substituents may be the same as or different from each other, and in one or more embodiments, examples thereof include a halogen atom, a cyano group, a trifluoromethyl group, a nitro group, a hydroxy group, a methylenedioxy group, a lower alkyl group, a lower alkoxy group, a benzyloxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanoylamino group, and a lower alkylsulfonamide group. In one or more embodiments, examples of the halogen atom include a fluorine atom, a chlorine atom, a bromine atom, and an iodine atom.

In Formulae (I) and (I'), $R^3$ represents a hydrogen atom, a linear, branched, or cyclic alkyl group having 1 to 6 carbon atoms, a benzyl or heteroarylmethyl group, a substituted or unsubstituted aryl group, a substituted or unsubstituted heteroaryl group, or $CH_2OC(O)R^4$—.

In Formulae (I) and (I'), $R^4$ represents a linear, branched, or cyclic alkyl group having 1 to 6 carbon atoms, a benzyl or heteroaryl methyl group, a substituted or unsubstituted aryl group, or a substituted or unsubstituted heteroaryl group.

In one or more embodiments, examples of the linear or branched alkyl group having 1 to 6 carbon atoms represented by $R^3$ and $R^4$ include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group. Also, in one or more embodiments, examples of the cyclic alkyl group having 1 to 6 carbon atoms represented by $R^3$ and $R^4$ include cyclopropyl, cyclobutyl, cyclopentyl, and cyclohexyl.

In one or more embodiments, examples of the heteroaryl (including heteroaryl of the heteroarylmethyl group) represented by $R^3$ and $R^4$ include a 5- to 6-membered monocyclic group having 1 to 2 nitrogen atoms, a 5- to 6-membered monocyclic group having 1 to 2 nitrogen atoms and either 1 oxygen atom or 1 sulfur atom, a 5-membered monocyclic group having 1 oxygen atom or 1 sulfur atom, and a bicyclic group that has 1 to 4 nitrogen atoms and is formed through fusion of a 6-membered ring and a 5- or 6-membered ring. Also, in another one or more embodiments, examples of the heteroaryl include 2-pyridyl, 3-pyridyl, 4-pyridyl, 2-thienyl, 3-thienyl, 3-oxadiazolyl, 2-imidazolyl, 2-thiazolyl, 3-isothiazolyl, 2-oxazolyl, 3-isoxazolyl, 2-furyl, 3-furyl, 3-pyrrolyl, 2-quinolyl, 8-quinolyl, 2-quinazolinyl, and 8-purinyl. Examples of the aryl group represented by $R^1$ and $R^2$ include an aryl group having 10 or less carbon atoms, such as a phenyl group or a naphthyl group.

The number of substituents of the aryl group and the heteroaryl group represented by $R^3$ and $R^4$ may be one or more, and the substituents may be the same as or different from each other, and in one or more embodiments, examples thereof include a halogen atom, a cyano group, a trifluoromethyl group, a nitro group, a hydroxy group, a methylenedioxy group, a lower alkyl group, a lower alkoxy group, a benzyloxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanoylamino group, and a lower alkylsulfonamide group. In one or more embodiments, examples of the halogen atom include a fluorine atom, a chlorine atom, a bromine atom, and an iodine atom.

In Formulae (I) and (I'), X represents a hydrogen atom, a halogen atom, an amino group, the above-described $R^1$- and $R^2$-substituted amino group, an azide group, a cyano group, a nitro group, a hydroxy group, a linear, branched, or cyclic alkyloxy group having 1 to 6 carbon atoms, a substituted or unsubstituted aryloxy group, a substituted or unsubstituted heteroaryloxy group, a mercapto group, a linear, branched, or cyclic alkylthio group having 1 to 6 carbon atoms, a substituted or unsubstituted arylthio group, a substituted or unsubstituted heteroarylthio group, a linear, branched, or cyclic alkyl group having 1 to 6 carbon atoms, a benzyl or heteroarylmethyl group, a substituted or unsubstituted aryl group, or a substituted or unsubstituted heteroaryl group.

In one or more embodiments, examples of the linear or branched alkyl group (including alkyl groups of the alkyloxy group and the alkylthio group) having 1 to 6 carbon atoms represented by X include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group. Also, in one or more embodiments, examples of the cyclic alkyl group having 1 to 6 carbon atoms represented by X include cyclopropyl, cyclobutyl, cyclopentyl, and cyclohexyl.

In one or more embodiments, examples of the heteroaryl (including heteroaryl of the heteroaryloxy group, the heteroarylthio group, and the heteroarylmethyl group) represented by X include a 5- to 6-membered monocyclic group having 1 to 2 nitrogen atoms, a 5- to 6-membered monocyclic group having 1 to 2 nitrogen atoms and either 1 oxygen atom or 1 sulfur atom, a 5-membered monocyclic group having 1 oxygen atom or 1 sulfur atom, and a bicyclic group that has 1 to 4 nitrogen atoms and is formed through fusion of a 6-membered ring and a 5- or 6-membered ring. Also, another or more embodiments, examples thereof include 2-pyridyl, 3-pyridyl, 4-pyridyl, 2-thienyl, 3-thienyl, 3-oxadiazolyl, 2-imidazolyl, 2-thiazolyl, 3-isothiazolyl, 2-oxazolyl, 3-isoxazolyl, 2-furyl, 3-furyl, 3-pyrrolyl, 2-quinolyl, 8-quinolyl, 2-quinazolinyl, and 8-purinyl. Examples of the aryl group (including heteroaryl of the aryloxy group and the arylthio group) represented by X include an aryl group having 10 or less carbon atoms, such as a phenyl group or a naphthyl group.

The number of substituents of the aryl group and the heteroaryl group represented by X may be one or more, and the substituents may be the same as or different from each other, and in one or more embodiments, examples thereof include a halogen atom, a cyano group, a trifluoromethyl group, a nitro group, a hydroxy group, a methylenedioxy group, a lower alkyl group, a lower alkoxy group, a benzyloxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanoylamino group, and a lower alkylsulfonamide group.

In one or more embodiments, examples of the halogen atom represented by X include a fluorine atom, a chlorine atom, a bromine atom, and an iodine atom.

In one aspect, the present disclosure relates to a pharmaceutical composition for preventing, ameliorating, suppressing progression of, and/or treating Fabry disease, the pharmaceutical composition containing, as an active ingredient, a compound represented by Formula (IX) or (IX'), a prodrug thereof, or a pharmaceutically acceptable salt thereof.

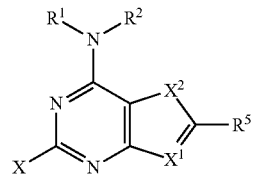

(IX)

-continued

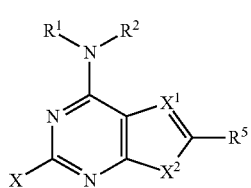
(IX')

R¹ and R² each independently represent a hydrogen atom, a linear, branched, or cyclic alkyl group having 1 to 6 carbon atoms, a benzyl or heteroarylmethyl group, a substituted or unsubstituted aryl group, or a substituted or unsubstituted heteroaryl group.

R⁵ represents a hydrogen atom, a halogen atom, a substituted or unsubstituted linear, branched, or cyclic alkoxy group having 1 to 6 carbon atoms.

X¹ represents N or CH.

X² represents —N(R³)—, S, or O.

R³ represents a hydrogen atom, a linear, branched, or cyclic alkyl group having 1 to 6 carbon atoms, a benzyl or heteroarylmethyl group, a substituted or unsubstituted aryl group, a substituted or unsubstituted heteroaryl group, or $CH_2OC(O)R^4$—.

R⁴ represents a $C_1$-$C_6$ alkyl group, a benzyl or heteroarylmethyl group, a substituted or unsubstituted aryl group, or a substituted or unsubstituted heteroaryl group.

X represents a hydrogen atom, a halogen atom, an amino group, an R¹- and R²-substituted amino group, an azide group, a cyano group, a nitro group, a hydroxy group, a linear, branched, or cyclic alkyloxy group having 1 to 6 carbon atoms, a substituted or unsubstituted aryloxy group, a substituted or unsubstituted heteroaryloxy group, a mercapto group, a linear, branched, or cyclic alkylthio group having 1 to 6 carbon atoms, a substituted or unsubstituted arylthio group, a substituted or unsubstituted heteroarylthio group, a linear, branched, or cyclic alkyl group having 1 to 6 carbon atoms, a benzyl or heteroarylmethyl group, a substituted or unsubstituted aryl group, or a substituted or unsubstituted heteroaryl group.

R¹, R², R³, R⁴, and X in Formulae (IX) and (IX') are the same as those in Formulae (I) and (I').

In one or more embodiments, examples of the alkoxy group having 1 to 6 carbon atoms represented by R⁵ include a methoxy group, an ethoxy group, a propoxy group, a butoxy group, a pentyloxy group, a hexyloxy group, a phenyloxy group, a cyclopropyloxy group, a cyclobutyloxyl group, a cyclopentyloxy group, and a cyclohexyloxy group.

The number of substituents of the alkoxy group represented by R⁵ may be one or more, and the substituents may be the same as or different from each other, and in one or more embodiments, examples thereof include a halogen atom, a cyano group, a trifluoromethyl group, a nitro group, a hydroxy group, a methylenedioxy group, a lower alkyl group, a lower alkoxy group, a benzyloxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanoylamino group, and a lower alkylsulfonamide group.

In one or more embodiments, examples of the halogen atom include a fluorine atom, a chlorine atom, a bromine atom, and an iodine atom.

In one aspect, the present disclosure relates to a pharmaceutical composition for preventing, ameliorating, suppressing progression of, and/or treating Fabry disease, the pharmaceutical composition containing, as an active ingredient, a compound represented by Formula (X) or (X'), a prodrug thereof, or a pharmaceutically acceptable salt thereof.

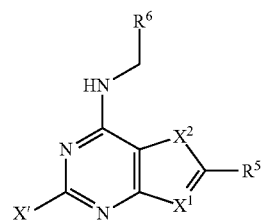
(X)

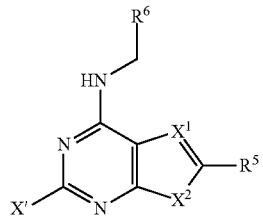
(X')

R⁵ represents a hydrogen atom, a methoxy group, or a 2,2,2-trifluoroethoxy group.

R⁶ represents a 2-furyl group, a 2-thiazolyl group, or a 4-pyridyl group.

X¹ represents N or CH.

X² represents NH, NCH₃, S, or O.

X' represents a hydrogen atom, a chlorine atom, an iodine atom, a bromine atom, or a fluorine atom.

In one or more embodiments, examples of the compound according to the present disclosure include the compounds below,

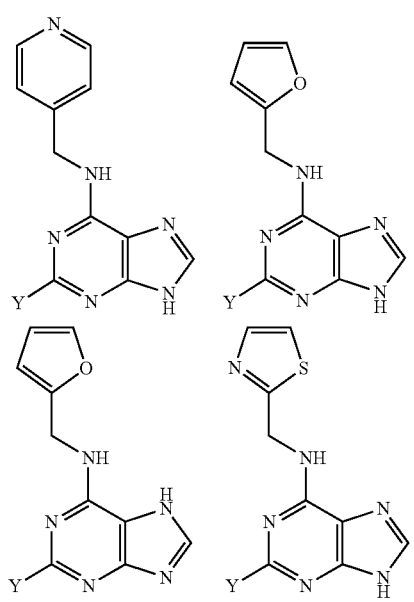

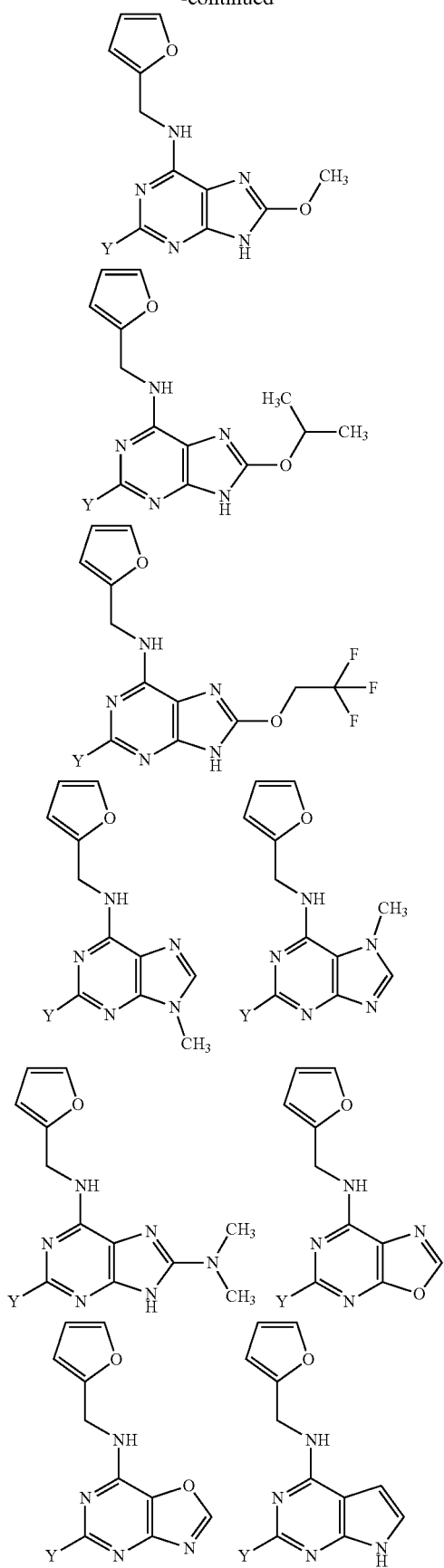
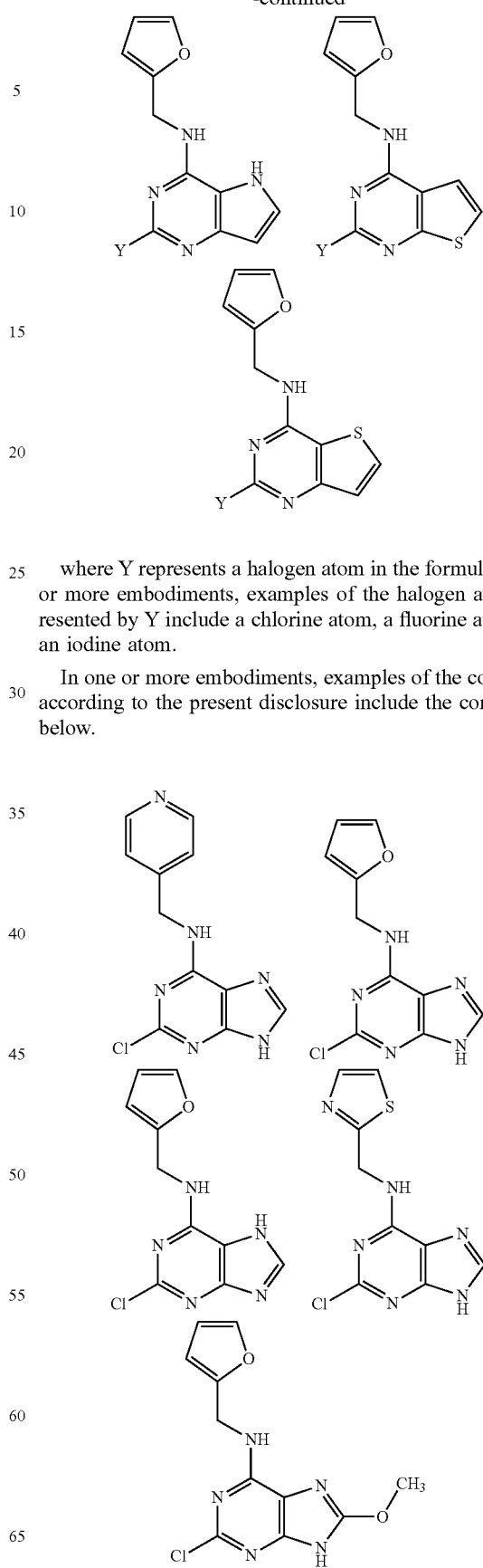
where Y represents a halogen atom in the formula. In one or more embodiments, examples of the halogen atom represented by Y include a chlorine atom, a fluorine atom, and an iodine atom.
In one or more embodiments, examples of the compound according to the present disclosure include the compounds below.

-continued

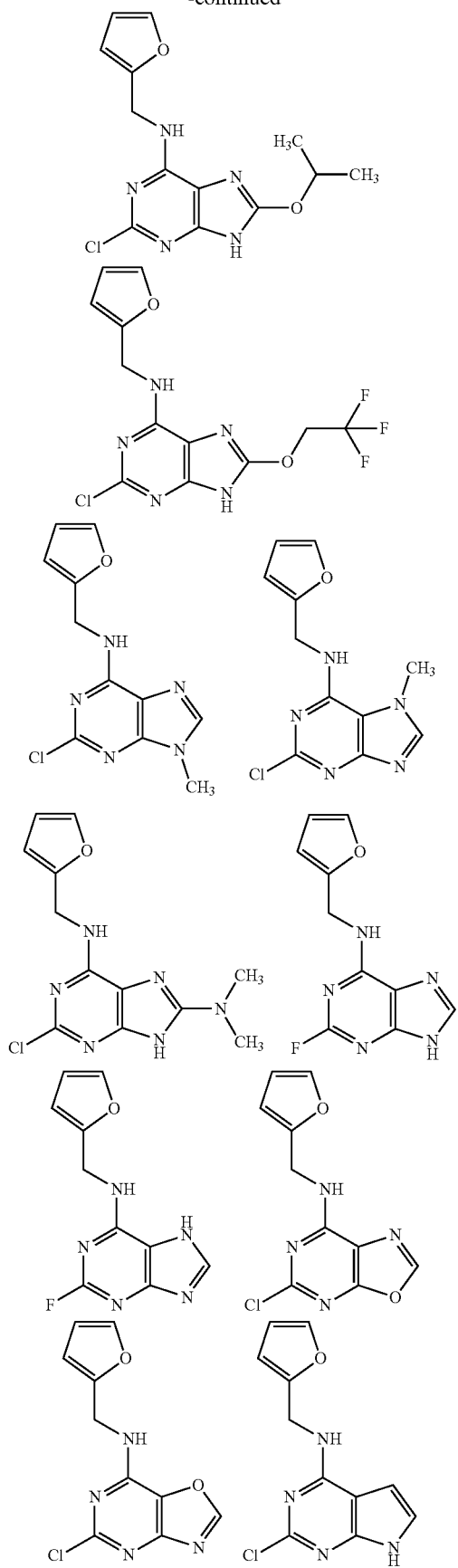

-continued

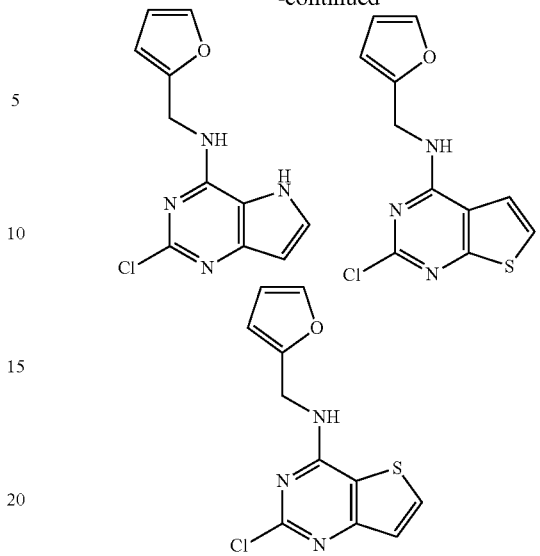

In the present disclosure, if $X^1$ and $X^2$ represent N and NH, Formulae (I) and (I'), (IX) and (IX'), and (X) and (X') above are each tautomers. Although only one tautomer is described in the above-described specific examples, disclosure of one tautomer also discloses the other tautomer in the present disclosure.

If the compound represented by Formula (I), (I'), (IX), (IX'), (X), or (X') includes an asymmetric carbon atom, and/or if stereoisomers thereof are present, the compound is a mixture of isomers or an isolated compound, in one or more embodiments.

The compound represented by Formula (I), (I'), (IX), (IX'), (X), or (X') in the present disclosure can be synthesized by referring to the method disclosed in WO2010/118367 or the method disclosed in WO2016/115434.

In one or more embodiments, a "prodrug" in the present disclosure refers to compounds that are to be converted in a living body into compounds represented by General Formula (I), (I'), (II), (II'), (III), (IV), (V), (VI), (VII), (VIII), (IX), (IX'), (X), or (X').

If a compound has a carboxyl group, examples of the prodrug include a compound whose carboxyl group has changed to an alkoxycarbonyl group, a compound whose carboxyl group has changed to an alkylthio carbonyl group, and a compound whose carboxyl group has changed to an alkylaminocarbonyl group. If a compound has an amino group, examples of the prodrug include a compound whose amino group is substituted with an alkanoyl group to form an alkanoylamino group, a compound whose amino group is substituted with an alkoxycarbonyl group to form an alkoxycarbonylamino group, a compound whose amino group has changed to an acyloxymethylamino group, and a compound whose amino group has changed to a hydroxylamine. If a compound has a hydroxy group, examples of the prodrug include a compound whose hydroxy group is substituted with the acyl group to form an acyloxy group, a compound whose hydroxy group has changed to a phosphoric acid ester, and a compound whose hydroxy group has changed to an acyloxymethyloxy group. An example of an alkyl portion of a group used to form these prodrugs is the alkyl group, and the alkyl group may be substituted (by an alkoxy group having 1 to 6 carbon atoms, for example). In one or more embodiments, examples of a compound whose carboxyl group has changed to an alkoxycarbonyl group include a lower (e.g., 1 to 6 carbon atoms) alkoxycarbonyl such as methoxycarbonyl and ethoxycarbonyl, and a lower (e.g., 1 to 6 carbon atoms) alkoxycarbonyl obtained through substitution with an alkoxy group, such as methoxymethoxycarbonyl, ethoxymethoxycarbonyl, 2-methoxyethoxycarbonyl, 2-methoxyethoxymethoxycarbonyl, and pivaloyloxymethoxycarbonyl.

In the present disclosure, a "pharmaceutically acceptable salt" refers to a pharmaceutically, pharmacologically, and/or medicinally acceptable salt, and examples thereof include inorganic acid salts, organic acid salts, inorganic base salts, organic base salts, and acidic or basic amino acid salts.

Preferred examples of the inorganic acid salts include hydrochloride, hydrobromide, sulfate, nitrate, and phosphate, and preferred examples of the organic acid salts include acetate, succinate, fumarate, maleate, tartrate, citrate, lactate, stearate, benzoate, methanesulfonate, and p-toluenesulfonate.

Preferred examples of the inorganic base salts include alkali metal salts such as sodium salts and potassium salts, alkaline earth salts such as calcium salts and magnesium salts, aluminum salts, and ammonium salts. Preferred examples of the organic base salts include diethylamine salts, diethanolamine salts, meglumine salts, and N', N-dibenzylethylenediamine salts.

Preferred examples of the acidic amino acid salts include aspartate and glutamate. Preferred examples of the basic amino acid salts include arginine salts, lysine salts, and ornithine salts.

In the present disclosure, a "salt of a compound" may include a hydrate that can be formed as a result of a compound being left in the air and absorbing moisture. Also, in the present disclosure, a "salt of a compound" may include a solvate that can be formed as a result of a compound absorbing a certain type of solvent.

In one or more embodiments, a known drug preparation technique may be applied to the pharmaceutical composition according to the present disclosure to have a dosage form that is suitable for an administration form. An example of the administration form is, but not limited to, oral administration via dosage forms such as tablets, capsules, granules, powders, pills, troches, syrups, and liquid formulations. Alternatively, an example of the administration form is parenteral administration via dosage forms such as injections, liquid formulations, aerosols, suppositories, plasters and pressure sensitive adhesives, cataplasms, lotions, liniments, ointments, and eye drops. Although these pharmaceutical preparations are not limited thereto, they may be manufactured using a known method using additives such as excipients, lubricants, binders, disintegrants, stabilizing agents, corrigents, and diluents.

In one or more embodiments, the pharmaceutical composition according to the present disclosure does not contain other active ingredients having a therapeutic effect, or contains another one or more active ingredients.

Examples of the excipient include, but not limited to, starches such as starch, potato starch, and corn starch, lactose, crystalline cellulose, and calcium hydrogen phosphate. Examples of the coating agent include, but not limited to, ethyl cellulose, hydroxypropyl cellulose, hydroxypropyl methylcellulose, shellac, talc, carnauba wax, and paraffin.

Examples of the binder include, but not limited to, polyvinylpyrrolidone, macrogol, and compounds that are similar to the above-described excipients.

Examples of the disintegrant include, but not limited to, compounds that are similar to those given as examples of the excipient, chemically-modified starches and celluloses such as croscarmellose sodium, sodium carboxymethyl starch, and crosslinked polyvinylpyrrolidone.

Examples of the stabilizing agent include, but not limited to, para-hydroxybenzoic acid esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid.

Examples of the corrigent include, but not limited to, sweeteners, acidulants, and flavors that are usually used.

Although there is no limitation on a solvent, ethanol, phenol, chlorocresol, purified water, distilled water, and the like can be used as a solvent to manufacture liquid formulations, and a surfactant, an emulsifying agent, or the like can also be used as needed. Examples of the surfactant or emulsifying agent include, but not limited to, polysorbate 80, polyoxyl 40 stearate, and lauromacrogol.

A method for using a pharmaceutical composition according to the present disclosure may change depending on the symptoms, age, administration method, and the like. Although there is no limitation on the usage method, a pharmaceutical composition can be intermittently or continuously administered orally, percutaneously, submucosally, subcutaneously, intramuscularly, intravascularly, intracerebrally, or intraperitoneally such that the concentration of the compound in the body that is an active ingredient and is represented by Formula (I) or (I') is in a range of 100 nM to 1 mM. In a non-limiting embodiment, in the case of oral administration, the pharmaceutical composition may be administered to a subject (an adult human if the subject is a human) in a dosage of 0.01 mg (preferably 0.1 mg) to 2000 mg (preferably 500 mg and more preferably 100 mg), which is expressed in terms of the compound represented by Formula (I) or (I'), once or over several times in a day according to a symptom. In a non-limiting embodiment, in the case of intravenous administration, the pharmaceutical composition may be administered to a subject (an adult human if the subject is a human) in a dosage of 0.001 mg (preferably 0.01 mg) to 500 mg (preferably 50 mg) once or over several times in a day according to a symptom.

Method and Use

In another aspect, the present disclosure may relate to the following methods:
  a method for altering splicing of a pre-mRNA of a mutant GLA gene having the IVS4+919G>A mutation in human cells or human individuals; and
  a method for increasing a ratio of normal splicing to splicing abnormality of a pre-mRNA of a mutant GLA gene having the IVS4+919G>A mutation in human cells or human individuals.

These methods may be performed by bringing the compound represented by Formula (I), (I'), (IX), (IX'), (X), or (X') or the pharmaceutical composition according to the present disclosure into contact with the human cells or the human individuals.

In one or more non-limiting embodiments, the compound represented by Formula (I), (I'), (IX), (IX'), (X) or (X') or the pharmaceutical composition according to the present disclosure may be brought into contact with in vitro or ex vivo human cells through addition of the compound represented by Formula (I), (I'), (IX), (IX'), (X) or (X'), a salt thereof, or the pharmaceutical composition according to the present disclosure to a cell culture medium. In one or more non-limiting embodiments, the addition is performed so that the concentration of the compound represented by Formula (I), (I'), (IX), (IX'), (X) or (X') is in a range of 100 nM to 1 mM. In one or more embodiments, the compound represented by Formula (I), (I'), (IX), (IX'), (X) or (X') or the pharmaceutical composition according to the present disclosure may be brought into contact with in vivo human cells and human individuals according to the method for use of the pharmaceutical composition as described above.

Thus, the present disclosure may further relate to one or more embodiments below.

[A1] A pharmaceutical composition for preventing, ameliorating, suppressing progression of, and/or treating Fabry disease, the pharmaceutical composition containing an active ingredient capable of suppressing a splicing abnormality that contributes to development or progression of the Fabry disease.

[A2] The pharmaceutical composition according to [A1], in which the splicing abnormality is a splicing abnormality that contributes to at least one of a GLA enzyme deficiency and a decrease in activity of the GLA enzyme.

[A3] The pharmaceutical composition according to [A1] or [A2], in which the splicing abnormality is a splicing abnormality caused by the IVS4+919G>A mutation in the GLA gene.

[A4] A pharmaceutical composition for preventing, ameliorating, suppressing progression of, and/or treating Fabry disease, the pharmaceutical composition containing, as an active ingredient, a compound represented by Formula (I) or (I'), a prodrug thereof, or a pharmaceutically acceptable salt thereof,

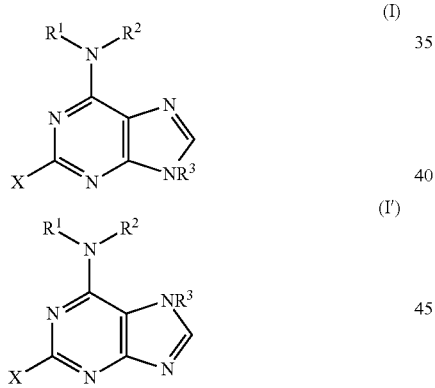

where, in Formulae (I) and (I'),
- $R^1$ and $R^2$ each independently represent a hydrogen atom, a linear, branched, or cyclic alkyl group having 1 to 6 carbon atoms, a benzyl or heteroarylmethyl group, a substituted or unsubstituted aryl group, or a substituted or unsubstituted heteroaryl group;
- $R^3$ represents a hydrogen atom, a linear, branched, or cyclic alkyl group having 1 to 6 carbon atoms, a benzyl or heteroarylmethyl group, a substituted or unsubstituted aryl group, a substituted or unsubstituted heteroaryl group, or $CH_2OC(O)R^4$—;
- $R^4$ represents a linear, branched, or cyclic alkyl group having 1 to 6 carbon atoms, a benzyl or heteroarylmethyl group, a substituted or unsubstituted aryl group, or a substituted or unsubstituted heteroaryl group; and
- X represents a hydrogen atom, a halogen atom, an amino group, an $R^1$- and $R^2$-substituted amino group, an azide group, a cyano group, a nitro group, a hydroxy group, a linear, branched, or cyclic alkyloxy group having 1 to 6 carbon atoms, a substituted or unsubstituted aryloxy group, a substituted or unsubstituted heteroaryloxy group, a mercapto group, a linear, branched, or cyclic alkylthio group having 1 to 6 carbon atoms, a substituted or unsubstituted arylthio group, a substituted or unsubstituted heteroarylthio group, a linear, branched, or cyclic alkyl group having 1 to 6 carbon atoms, a benzyl or heteroarylmethyl group, a substituted or unsubstituted aryl group, or a substituted or unsubstituted heteroaryl group.

[A5] A pharmaceutical composition for preventing, ameliorating, suppressing progression of, and/or treating Fabry disease, the pharmaceutical composition containing, as an active ingredient, a compound represented by Formula (IX) or (IX'), a prodrug thereof, or a pharmaceutically acceptable salt thereof,

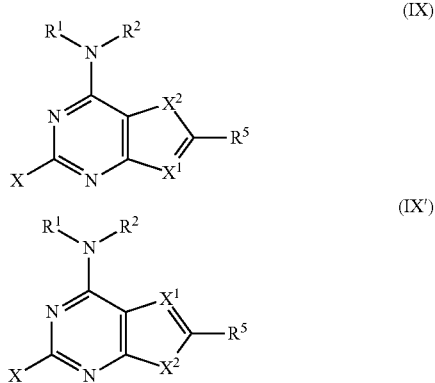

where, in Formulae (IX) and (IX'),
- $R^1$ and $R^2$ each independently represent a hydrogen atom, a linear, branched, or cyclic alkyl group having 1 to 6 carbon atoms, a benzyl or heteroarylmethyl group, a substituted or unsubstituted aryl group, or a substituted or unsubstituted heteroaryl group;
- $R^5$ represents a hydrogen atom, a halogen atom, a substituted or unsubstituted linear, branched, or cyclic alkoxy group having 1 to 6 carbon atoms;
- $X^1$ represents N or CH;
- $X^2$ represents —$N(R^3)$—, S, or O;
- $R^3$ represents a hydrogen atom, a linear, branched, or cyclic alkyl group having 1 to 6 carbon atoms, a benzyl or heteroarylmethyl group, a substituted or unsubstituted aryl group, a substituted or unsubstituted heteroaryl group, or $CH_2OC(O)R^4$—;
- $R^4$ represents a $C_1$-$C_6$ alkyl group, a benzyl or heteroarylmethyl group, a substituted or unsubstituted aryl group, or a substituted or unsubstituted heteroaryl group; and
- X represents a hydrogen atom, a halogen atom, an amino group, an $R^1$- and $R^2$-substituted amino group, an azide group, a cyano group, a nitro group, a hydroxy group, a linear, branched, or cyclic alkyloxy group having 1 to 6 carbon atoms, a substituted or unsubstituted aryloxy group, a substituted or unsubstituted heteroaryloxy group, a mercapto group, a linear, branched, or cyclic alkylthio group having 1 to 6 carbon atoms, a substituted or unsubstituted arylthio group, a substituted or unsubstituted heteroarylthio group, a linear, branched, or cyclic alkyl group having 1 to 6 carbon atoms, a benzyl or heteroarylmethyl group, a substituted or unsubstituted aryl group, or a substituted or unsubstituted heteroaryl group.

[A6] A pharmaceutical composition for preventing, ameliorating, suppressing progression of, and/or treating Fabry disease, the pharmaceutical composition containing, as an active ingredient, a compound represented by Formula (X) or (X') below, a prodrug thereof, or a pharmaceutically acceptable salt thereof,

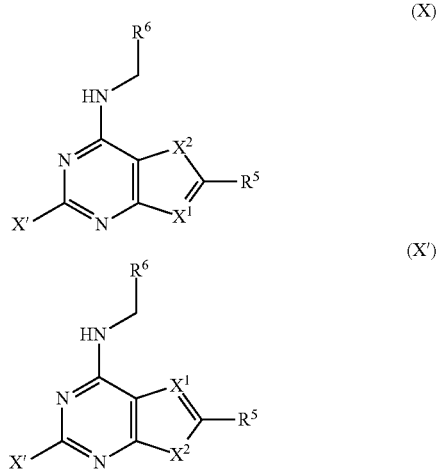

where, in Formulae (X) and (X'),
- $R^5$ represents a hydrogen atom, a halogen atom, a methoxy group, or a 2,2,2-trifluoroethoxy group;
- $R^6$ represents a 2-furyl group, a 2-thiazolyl group, or a 4-pyridyl group;
- $X^1$ represents N or CH;
- $X^2$ represents NH, NCH$_3$, S, or O; and
- X' represents a hydrogen atom, a chlorine atom, an iodine atom, a bromine atom, or a fluorine atom.

[A7] The pharmaceutical composition according to any of [A1] to [A6] for:
- altering splicing of a pre-mRNA of a mutant GLA gene having an IVS4+919G>A mutation in human cells or human individuals; or
- increasing a ratio of normal splicing to splicing abnormality of a pre-mRNA of a mutant GLA gene having the IVS4+919G>A mutation in human cells or human individuals.

[A8] A method for preventing, ameliorating, suppressing progression of, and/or treating Fabry disease, the method including
- administering the pharmaceutical composition according to any of [A1] to [A7] to a subject that requires the pharmaceutical composition.

[A9] A method for altering splicing of a pre-mRNA of a mutant GLA gene having an IVS4+919G>A mutation in human cells or human individuals, or
- a method for increasing a ratio of normal splicing to splicing abnormality of a pre-mRNA of a mutant GLA gene having the IVS4+919G>A mutation in human cells or human individuals, the method including
- bringing the pharmaceutical composition according to any of [A1] to [A7] into contact with the cells.

[A10] Use of the pharmaceutical composition according to any of [A1] to [A7] in the method according to [A8] or [A9].

[A11] Use of the compound defined in [A4] for manufacturing the pharmaceutical composition according to any of [A1] to [A7], a prodrug thereof, or a pharmaceutically acceptable salt thereof.

Pharmaceutical Composition Capable of Preventing or Ameliorating GLA Deficiency or Decrease in GLA Activity In one or more embodiments, the present disclosure relates to a pharmaceutical composition for diseases of which GLA deficiency contributes to the development or progression thereof, the pharmaceutical composition containing an active ingredient capable of suppressing the splicing abnormality.

In another one or more embodiments, the present disclosure relates to a pharmaceutical composition for diseases of which GLA deficiency contributes to the development or progression thereof, the pharmaceutical composition containing, as an active ingredient, the compound represented by Formula (I), (I'), (IX), (IX'), (X), or (X'), a prodrug thereof, or a pharmaceutically acceptable salt thereof Pharmaceutical Composition for Cystic Fibrosis The inventors of the present invention made a new discovery that the compounds represented by Formulae (III), (VII), and (VIII) suppress pseudo exon resulting from the 3849+10kbC>T mutation in the CFTR gene in cystic fibrosis, and as a result of which normal CFTR splicing products are restored.

In another aspect, the present disclosure relates to a pharmaceutical composition for preventing, ameliorating, suppressing progression of, and/or treating cystic fibrosis, the pharmaceutical composition containing, as an active ingredient, a compound represented by Formula (III), (VI), (VII), or (VIII), a prodrug thereof, or a pharmaceutically acceptable salt thereof, and a method therefor. Also, in another aspect, the present disclosure relates to a method for preventing, ameliorating, suppressing progression of, and/or treating cystic fibrosis, in which a compound represented by Formula (III), (VI), (VII), or (VIII), a prodrug thereof, or a pharmaceutically acceptable salt thereof is included as an active ingredient.

EXAMPLES

Hereinafter, although the present disclosure will be described in more detail byway of examples, these are illustrative, and the present disclosure is not limited to these examples. Note that all of the references cited in the present disclosure is incorporated as a portion of the present disclosure.

Manufacturing Example 1: Manufacture of Compound 1

Compound 1

Compound 1 was synthesized in the following manner with reference to the method disclosed in WO2010/118367.

Triethylamine (0.15 mL, 1.08 mmol) was added at room temperature to an acetonitrile (20 mL) solution containing 2,6-dichloro-1H-purine (189 mg, 1.00 mmol, commercial product) and furfurylamine (97.0 mg, 1.00 mmol, commercial product). The mixture was stirred at room temperature for 6 hours, and then stirred at 60° C. for 3 hours. After this mixed solution was concentrated under reduced pressure, water was added to the solution to form white precipitates, and the white precipitates were removed through filtration. The resultant solid was washed with water and subsequently with diethyl ether, and 2-chloro-N-(2-furanylmethyl)-7H-purin-6-amine (Compound 1) (19.8 mg, 0.0795 mmol, 8.0%) was obtained as a white solid.

TLC Rf 0.22 (ethyl acetate); $^1$H NMR (DMSO-d$_6$, 400 MHz) δ 4.56-4.67 (br, 2H), 6.24-6.28 (br, 1H), 6.35-6.40 (br, 1H), 7.54-7.57 (br, 1H), 8.11-8.15 (br, 1H), 8.54-8.64 (br, 1H), 13.05-13.17 (br, 1H).

Manufacturing Example 2

Compounds shown in Table 1 below were synthesized with reference to Manufacturing Example 1 and the method disclosed in WO2010/118367.

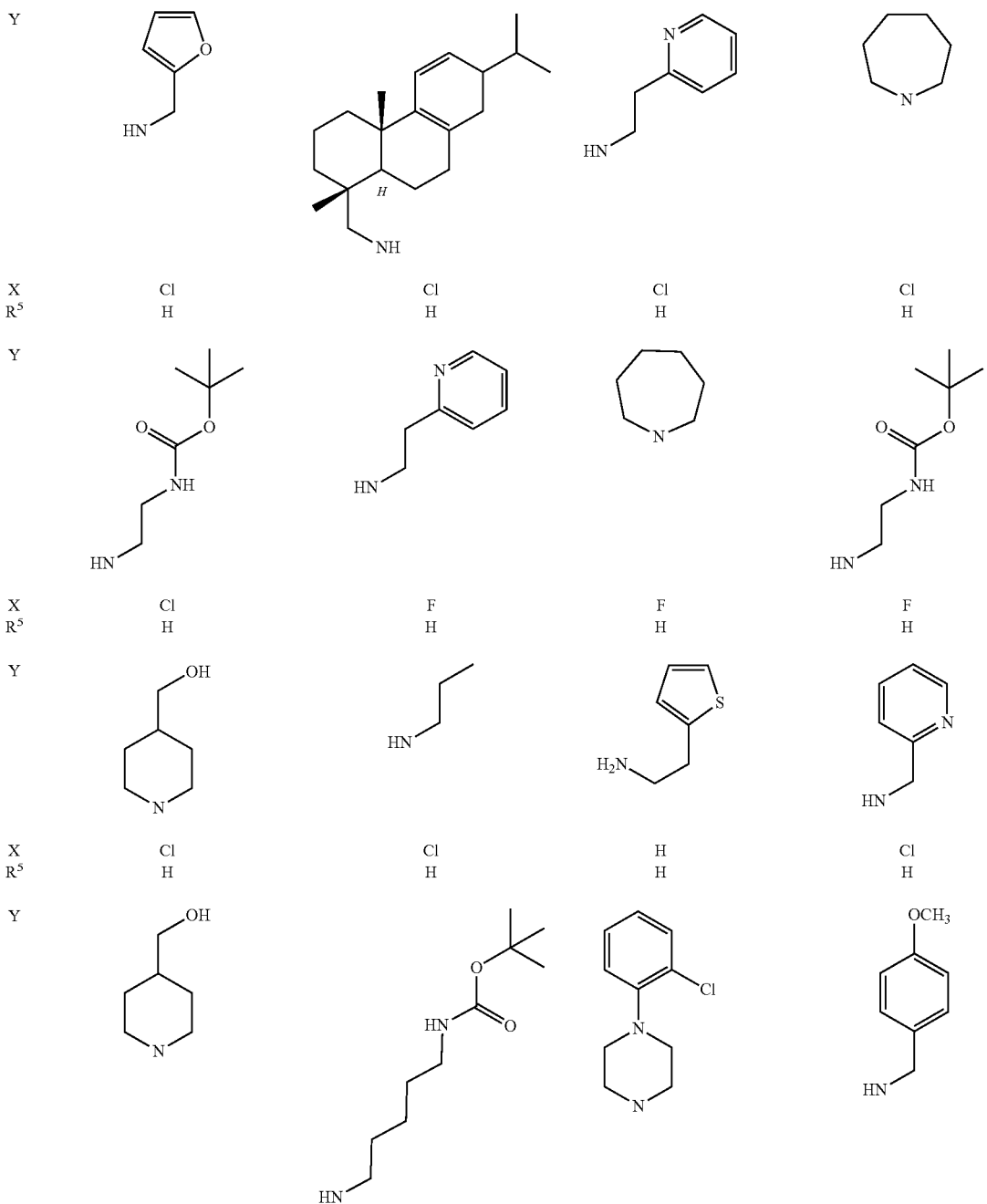

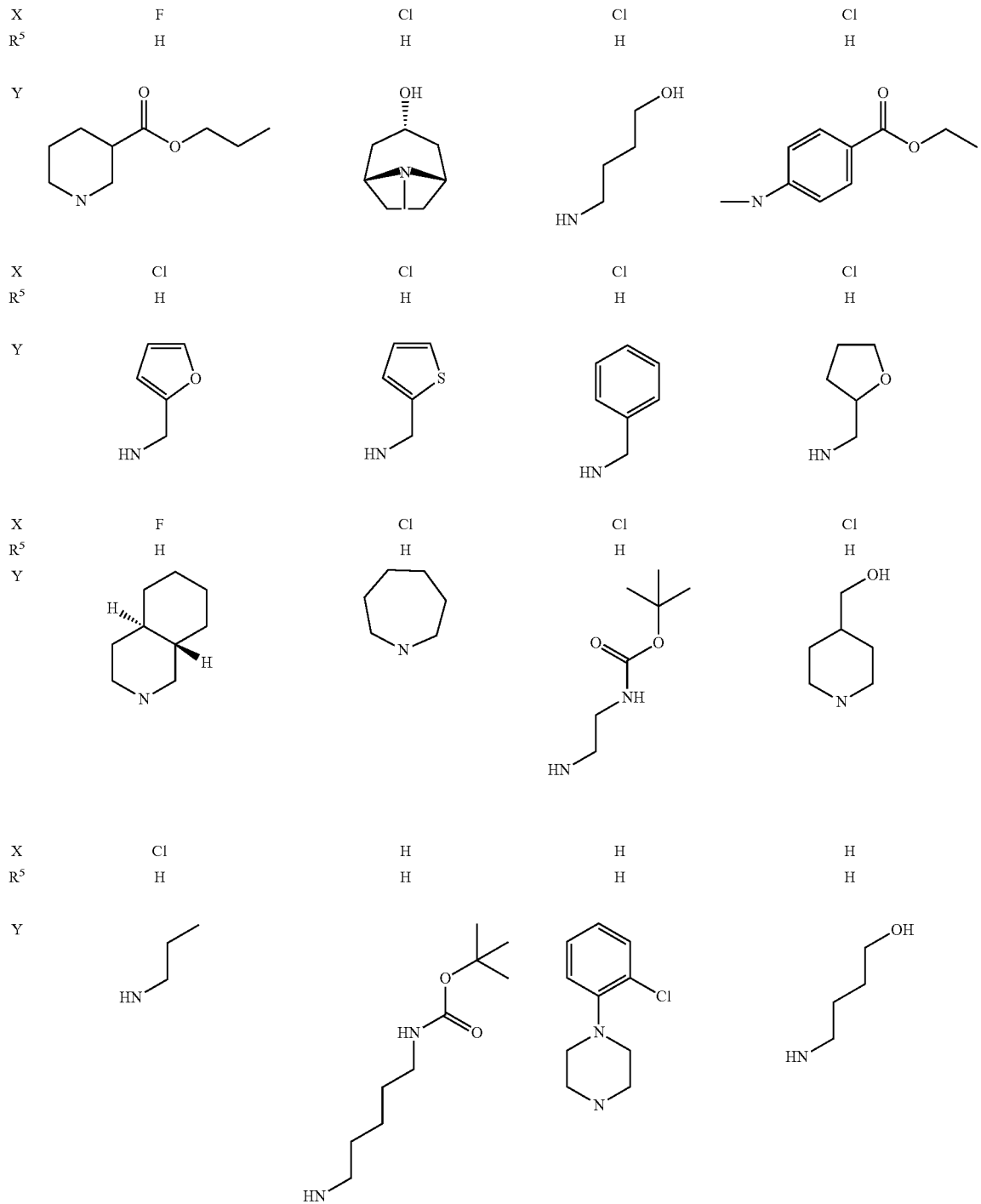

-continued
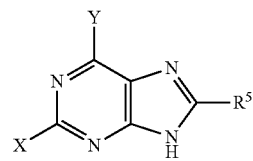
| X | H | H | H | H |
|---|---|---|---|---|
| R⁵ | H | H | H | H |
| Y | 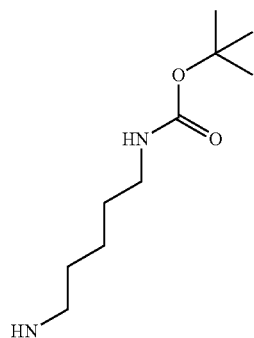 | 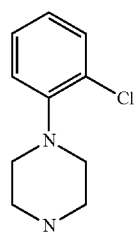 | 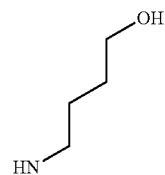 | 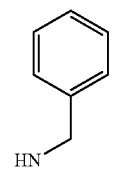 |
| X | F | F | F | H |
|---|---|---|---|---|
| R⁵ | H | H | H | H |
| Y | 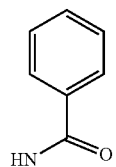 | 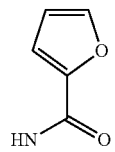 | 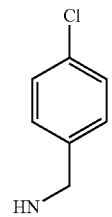 | 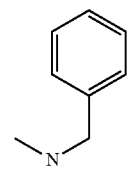 |
| X | H | H | H | H |
|---|---|---|---|---|
| R⁵ | H | H | H | H |
| Y | 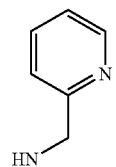 | 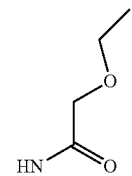 | 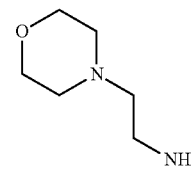 | 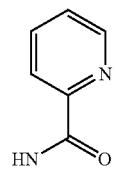 |
| X | H | H | H | H |
| R⁵ | H | H | H | H |

Manufacturing Example 3

Compounds shown in Table 2 below were synthesized with reference to the method disclosed in WO2010/010797.

TABLE 2

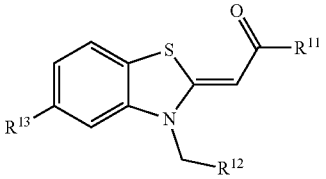

| $R^{11}$ | CH₃ | CH₃ | CH₃ | CH₃ | CH₃ | CH₃ |
|---|---|---|---|---|---|---|
| $R^{12}$ | CH₃ | CH₃ | CH₃ | CH₃ | CH₃ | CH₃ |
| $R^{13}$ | H | CH₃ | CH₃O | F | C₂H₅O | 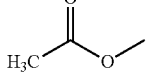 |
| $R^{11}$ | CH₃ | CH₃CH₃ | CH₃CH₃ | CH₃CH₃ | 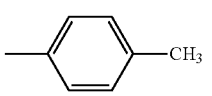 | |
| $R^{12}$ | 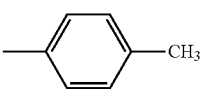 | CH₃ | CH₃ | 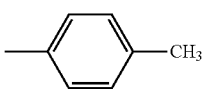 | CH₃ | |
| $R^{13}$ | CH₃O | H | CH₃O | CH₃O | CH₃O | |

Manufacturing Example 4

Compounds VIII-A to VIII-O below were synthesized with reference to the method disclosed in WO2017/175842.

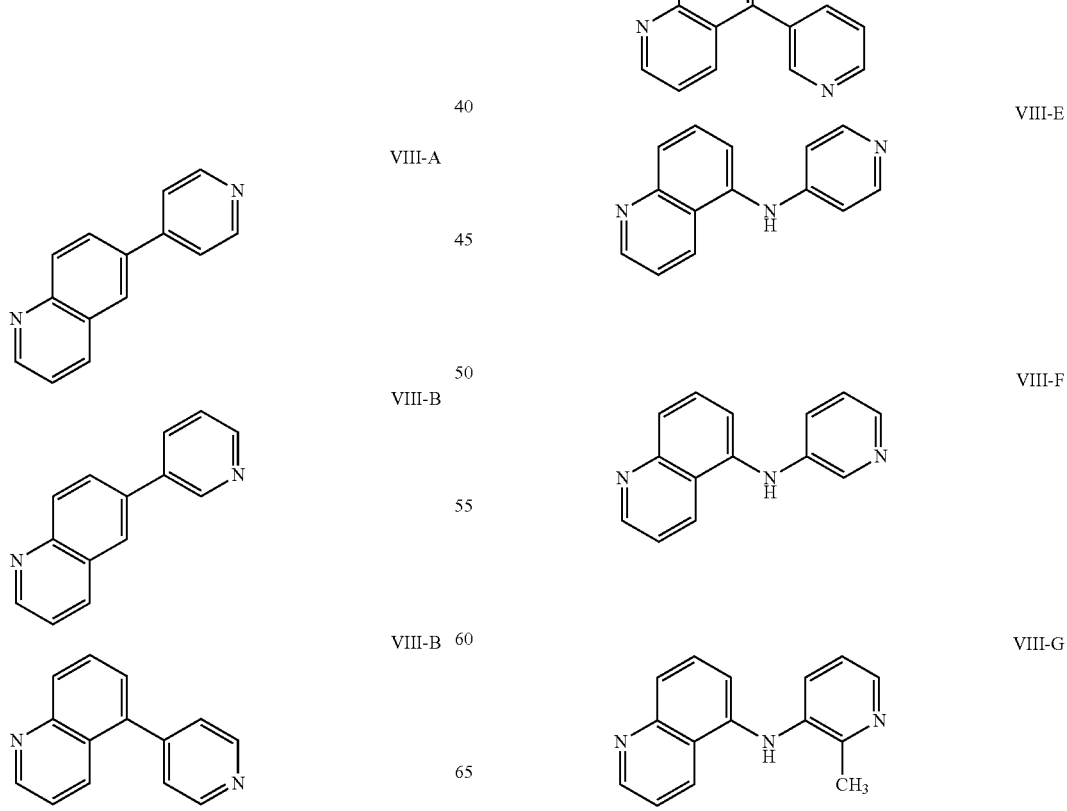

-continued

VIII-H

VIII-I

VIII-J

VIII-K

VIII-I

VIII-M

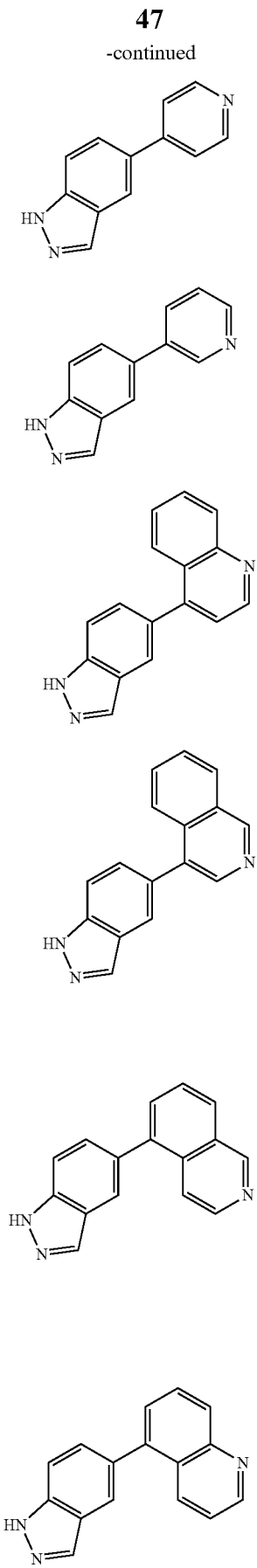

-continued

VIII-N

VIII-O

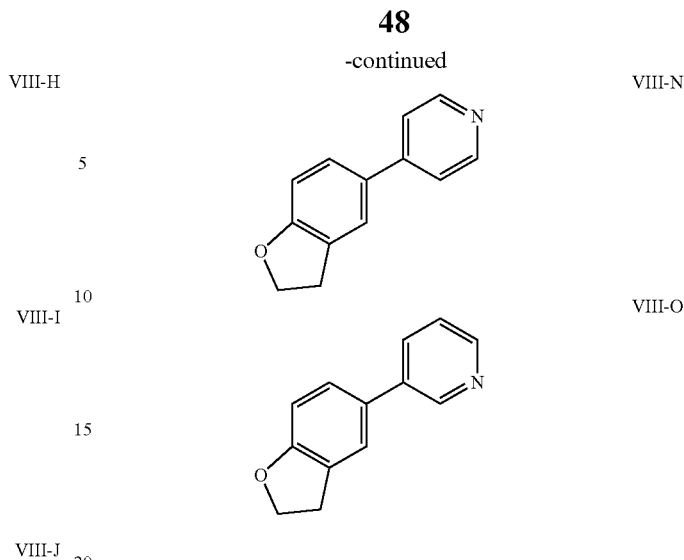

System for Evaluating Splicing Abnormality Caused by the GLA IVS4+919G>A Mutation in Fabry Disease A region starting from GLA exon 4 to exon5 (nt 7272-9215 in a GLA gene sequence) having anormal IVS4 or the IVS4+919G>A mutation downstream of a cytomegalovius (CMV) early gene promoter was cloned, and vectors pAM1 (wild-type IVS4) and pAM2 (the IVS4+919 G>A mutant) that serve as evaluations systems were produced (FIG. 2), for investigating the effects of a splicing operation compound on a splicing abnormality caused by the GLA IVS4+919G>A mutation. Splicing abnormalities (inclusion of the pseudo exon) in Fabry disease patient cells were demonstrated by introducing these vectors into culture cells, and therapeutic effects of the compounds were determined.

Figure 2:
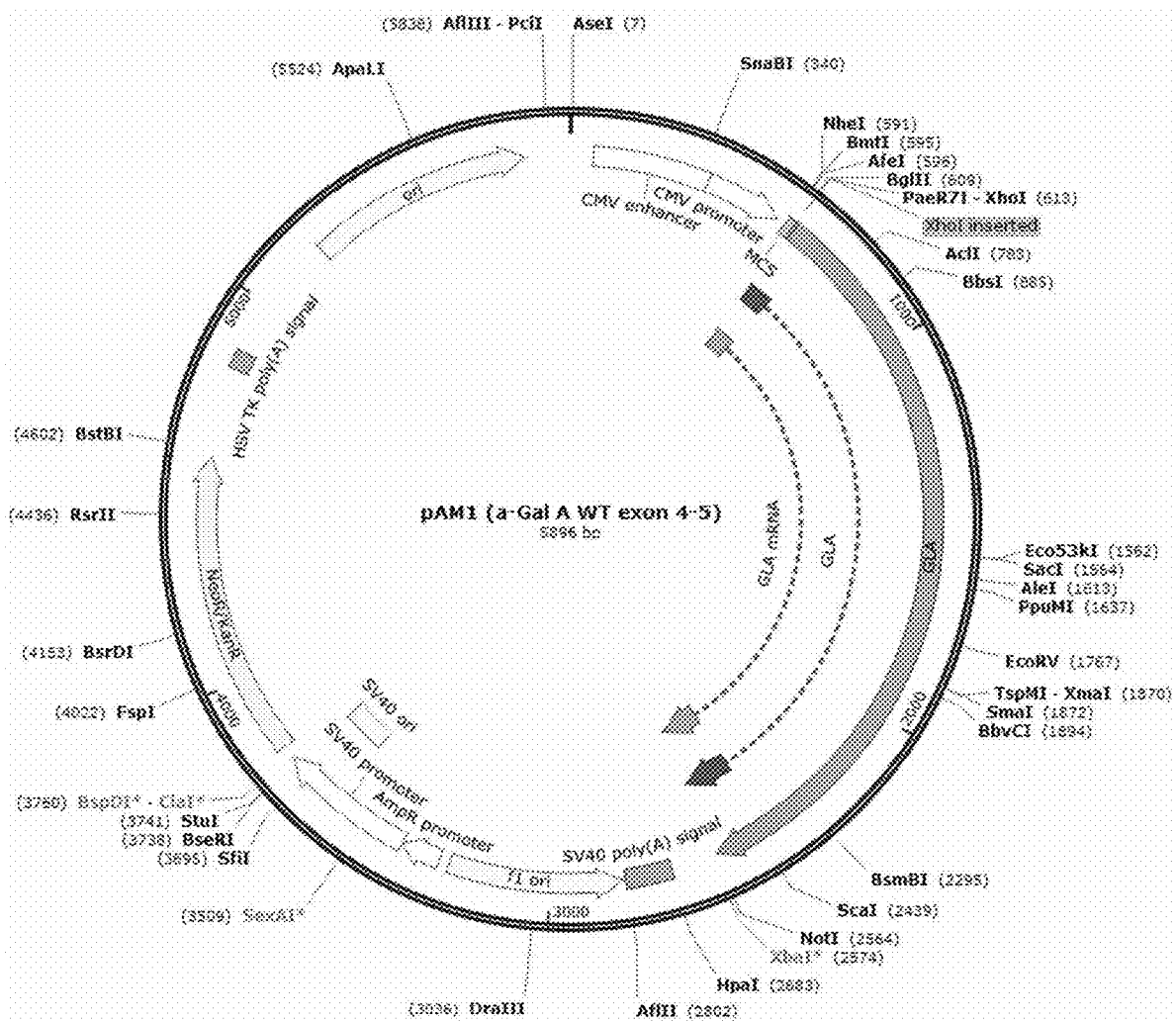
FIG. 2 is a diagram illustrating a GLA gene pseudo exon skipping evaluation system vector. pAM1 is constituted by a normal IVS4 sequence, and pAM2 has the IVS4+919G>A mutation. A precursor mRNA (pre-mRNA) including exon 4 to exon 5 is transcribed, and splicing alteration in patient cells with the identical mutation is recapitulated. pAM1 and pAM2 share sequences other than the sequence of the IVS4+919G>A point mutation.

The GLA gene pseudo exon skipping evaluation vector is shown in FIG. 2.

As shown in FIG. 2, pAM1 is constituted by a normal IVS4 sequence, and pAM2 has the IVS4+919G>A mutation. A precursor mRNA including exon 4 to exon 5 is transcribed, and splicing alteration recapitulating patient cells with the same mutation is demonstrated. Sequences of pAM1 and pAM2 other than the IVS4+919G>A point mutation were the same.

Confirmation of Effect of Compound 1 in Suppression of the Pseudo Exon Splicing of GLA Gene Caused by the IVS4+919G>A HeLa cells of human epithelial origin were cultured on 6 cm-plates ($0.5 \times 10^6$ cells), and the vectors shown in FIG. 2 were introduced into cells using lipofection reagents. Compound 1 was added at a concentration of 0 μM, 5 μM, or 10 μM, 4 hours after the vector transfection (final concentration of DMSO was 0.10%). Cellular RNA was collected 24 hours after the Compound 1 treatment, and treated with DNase to be applied for RT-PCR for evaluation of the alternative splicing of GLA gene. Results thereof are shown in FIGS. 3A and 3B.

Figure 3A:
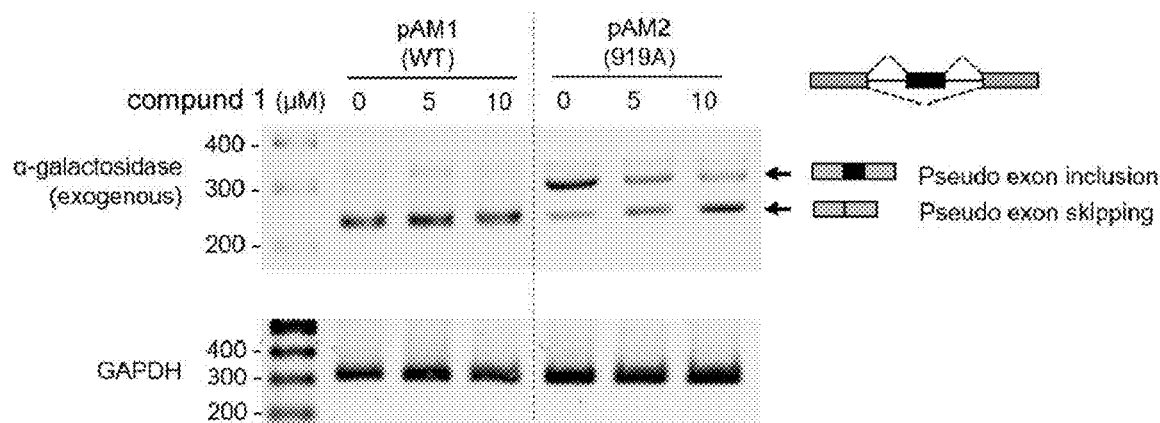
FIGS. 3A and 3B show one example of the effect of administration of Compound 1 on inhibiting the GLA gene pseudo exon in Fabry disease caused by the IVS4+919G>A mutation.
Figure 3B:
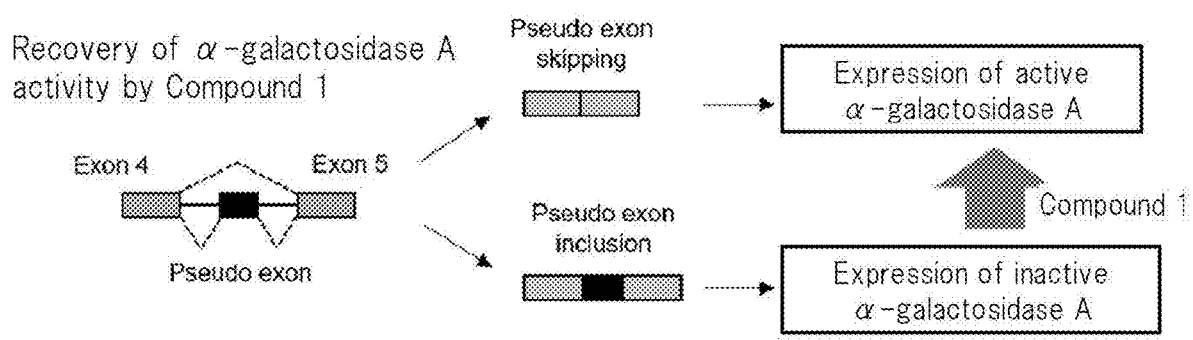

FIGS. 3A and 3B show the effect of Compound 1 through administration on inhibition of the GLA gene pseudo exon caused by the IVS4+919G>A mutation in Fabry disease. FIG. 3A shows results of RT-PCR for GLA gene with wild-type or VS4+919G>A mutant IVS4. The production of a normal isoform (pseudo exon skipping) was restored following Compound 1 treatment. The lower panel of FIG. 3A shows Glyceraldehyde 3-phosphate dehydrogenase (GAPDH) served as an internal control for RNA applied to RT-PCR and the amounts of RNA used in analysis are equal to each other. FIG. 3B is a schematic diagram illustrating GLA splicing control and recovery of the active enzyme using Compound 1.

As shown in FIG. 3A, Compound 1 suppressed aberrant splicing (incorporation of the pseudo exon) of GLA gene at a concentration as low as 5 μM. In addition, splice correcting activity of Compound 1 was observed in a concentration-dependent manner.

Figure 4A:
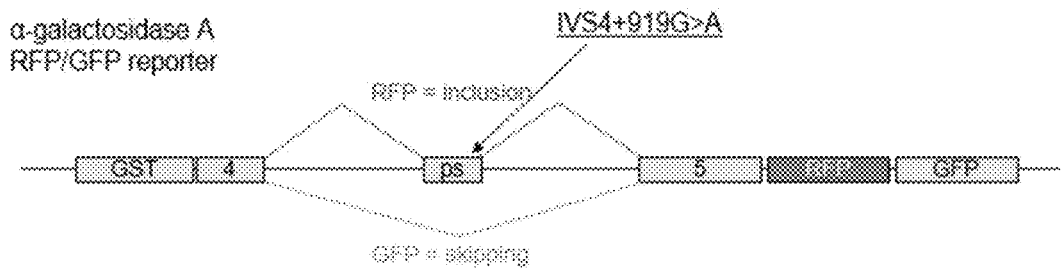
FIGS. 4A, 4B and 4C show one example of the effect of administration of Compound 1 on inhibiting the GLA gene pseudo exon in Fabry disease caused by the IVS4+919G>A mutation.

Then, a SPREADD reporter system, which is a system such that shown in FIG. 4A, that is capable of visualization and quantitative analysis of splicing alteration in living cells for GLA gene splicing, was newly constructed. In this reporter system, a red fluorescent protein (REP) is expressed if a pseudo exon is incorporated, and a green fluorescent protein (GFP) is expressed if a pseudo exon is skipped.

Figure 4B:
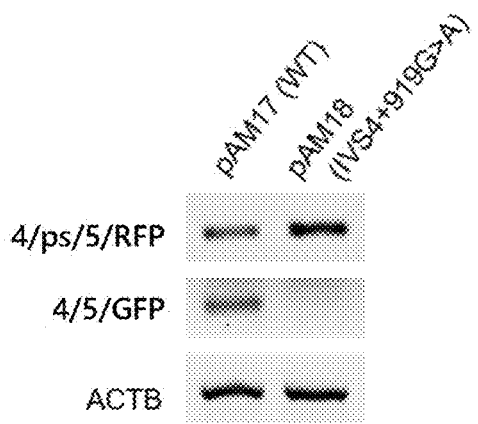

HeLa cells were transfected with the SPREADD reporter vectors, and as shown in FIG. 4B, pseudo exon skipping products (4/5/GFP) were dominantly expressed in the cells transfected with the SPREADD vector with wild-type IVS4 (pAM17 (WT)), while pseudo exon inclusion products (4/ps/5/RFP) were dominant when cells were transfected with the SPREADD vector with the IVS4+919 G>A mutation (pAM18 (IVS4+919 G>A)).

Figure 4C:
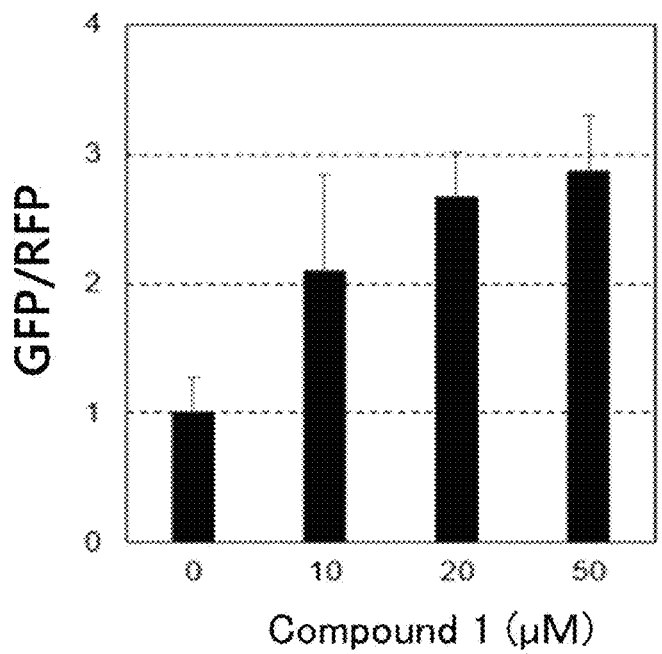

HeLa cells transfected with the SPREADD reporter pAM18 (IVS4+919 G>A mutant) were treated with Compound 1 (concentrations: 10 μM, 20 μM, and 50 μM) for 24 hours, and analyzed for fluorescent intensities of GFP and RFP for the GLA splicing. Results thereof are shown in FIG. 4C. The graph shown in FIG. 4C shows the relationship between the administration concentration and the fluorescence intensity ratio (GFP/RFP) of the control (solvent alone) and Compound 1. As shown in FIG. 4C, GFP/RFP of Compound 1 increased in a concentration-dependent manner. Thus, Compound 1 suppressed the pseudo exon of GLA gene, caused by the IVS4+919 G>A splicing mutation in a concentration-dependent manner.

Inclusion of the pseudo exon is a direct cause of a decrease in the GLA activity in cardiac Fabry disease. Thus, the above-described results indicates evidence of expected recovery of the GLA enzyme activity and therapeutic potential for cardiac Fabry disease by Compound 1.

Figure 5:
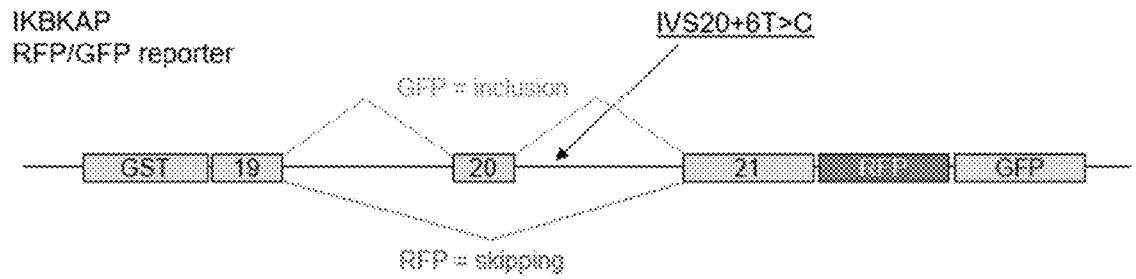
FIG. 5 is a diagram illustrating one example of the configuration of a SPREADD reporter system for a splicing mutation in the IKBKAP gene in familial dysautonomia.

Confirmation of the Suppressing Activity of the Aberrant Splicing (Exon Skipping) Caused by the IVS20+6T>C Splicing Mutation of IKBKAP Gene The SPREADD reporter system as shown in FIG. 5 for a splicing mutation in the IKBKAP gene in familial dysautonomia was produced. In the reporter system, GFP is expressed if the transcription product from the reporter vector is subjected to a normal splicing (exon 19/20/21), whereas RFP is expressed if the transcription product from the reporter vector subjected to an abnormal splicing (exon 19/21).

HeLa cells transfected with the SPREADD reporter construct were brought into contact with the compounds shown in Table 3 and cultured (concentration: 10 μM or 50 μM), and cellular fluorescence was measured after 24 hours. As a result, with regard to the compounds shown in Table 3 below, the relative GFP intensities over RFP (GFP/RFP) was higher than control (DMSO), confirming suppression effect of the exon 20 skipping of IKBKAP gene with the IVS20+6T>C mutation. Thus, the compounds represented by Formula (II), such as Compound 1, was capable of suppressing abnormal splicing resulting from the IVS20+6T>C mutation.

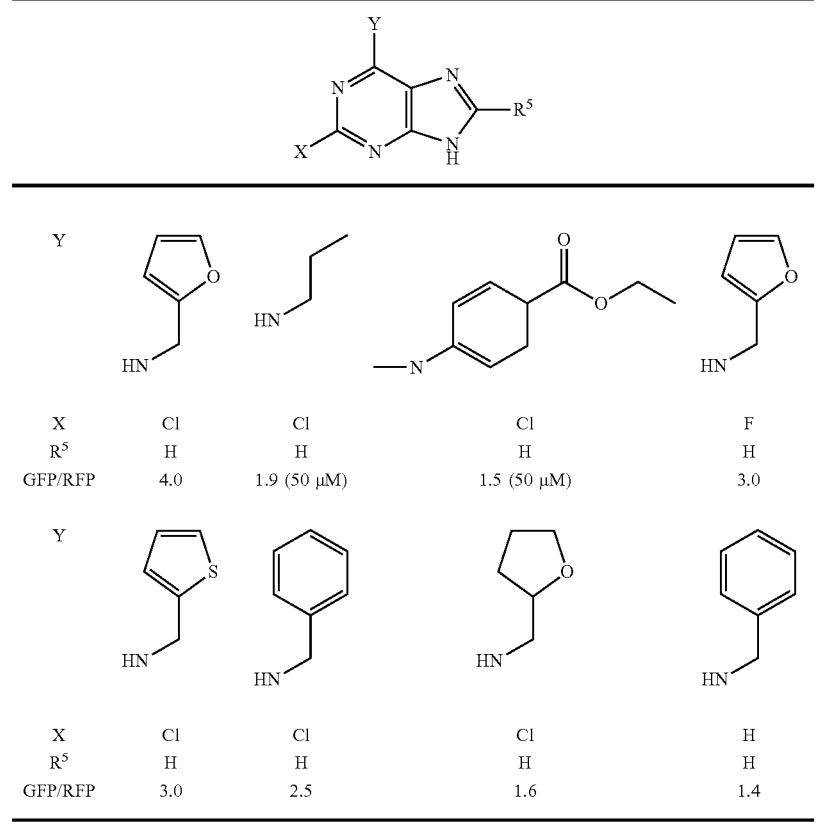

* control (DMSO): GFP/RFP 1.0

Confirmation of the Suppressive Effect on the Pseudo Exon-Type Mis-Splicing Caused by the c.3849+10kbC>T Splicing Mutation of CFTR Gene.

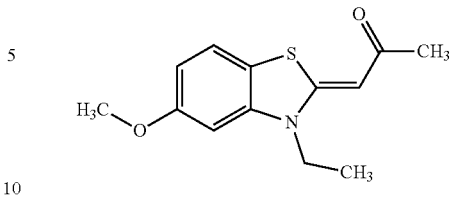

Compound III-1

Figure 6A:
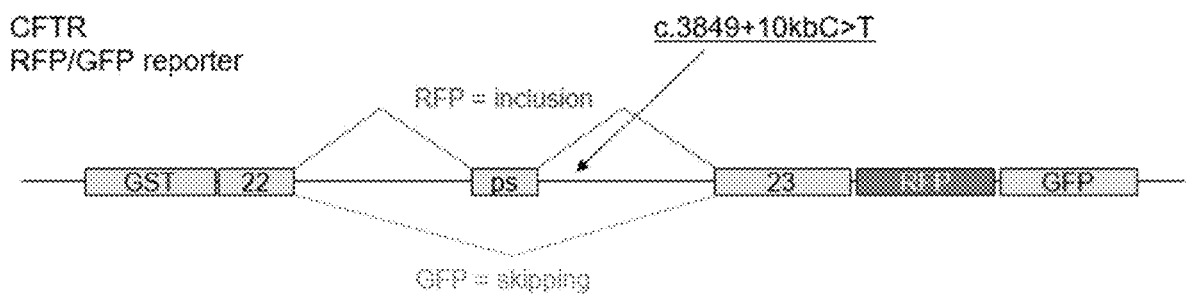
FIGS. 6A and 6B show one example of the effect of administration of Compound III-1 on inhibiting a CFTR gene pseudo exon in cystic fibrosis.

The SPREADD reporter system as shown in FIG. 6A that is a system capable of visualization and quantitative analysis of the splicing alteration in living cells for CFTR gene splicing in cystic fibrosis was produced. In the reporter system, RFP is expressed if the pseudo exon within the intron 22, caused by the c.3849+10kb C>T is included in the mRNA, whereas GFP is expressed if the pseudo exon is skipped.

HEK293 cells transfected with the SPREADD reporter construct were brought into contact with Compound III-1 and cultured (concentrations: 10 μM and 30 μM). Fluorescence observation was performed after 6 hours. Results thereof are shown in FIG. 6B.

Figure 6B:
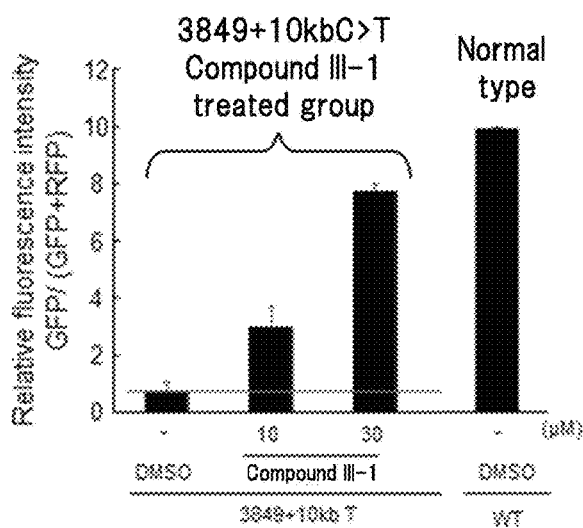

The graph shown in FIG. 6B shows the relationship between the administration concentration and the fluorescence intensity ratio (GFP/(GFP+RFP)) of the control (solvent alone) and Compound III-1. The results of HEK293 cells transfected with the normal reporter construct are also shown. As shown in FIG. 6B, GFP/(GFP+RFP) of Compound III-1 increased in a concentration-dependent manner. Also, if the concentration was 30 μM, the fluorescence intensity ratio was at about the same level as that of the normal type. Thus, the pseudo exon caused by the 3849+10kbC>T mutation in the CFTR gene was suppressed by Compound III-1 in a concentration-dependent manner, and as a result, the normal CFTR splicing products was restored.

Similar examinations were performed using the compounds shown in the following table, instead of Compound III-1 (concentration: 10 μM). Results thereof are shown in Table 4 below.

TABLE 4

| structure | | | |
|---|---|---|---|
| Fold change | 6.5 | 3.4 | 2 |
| S.D. | 2.3 | 4.4 | 3 |
| p-value (recovery rate) | <0.01 | >0.05 | >0.05 |
| structure | | | |
| Fold change | 0.6 | 2.4 | 0.6 |
| S.D. | 1.2 | 3.3 | 0.9 |
| p-value (recovery rate) | >0.05 | >0.05 | >0.05 |
| structure | | | |
| Fold change | 1.9 | 1.7 | 12.9 |
| S.D. | 1.7 | 0.4 | 1.7 |
| p-value (recovery rate) | >0.05 | >0.05 | <0.01 |

TABLE 4-continued

| structure | | | |
|---|---|---|---|
| Fold change | 1.9 | 2.4 | 0 |
| S.D. | 1.7 | 0.7 | 0 |
| p-value (recovery rate) | >0.05 | >0.05 | >0.05 |
| structure | | | |
| Fold change | 4.2 | 4.4 | 4.1 |
| S.D. | 3.6 | 4.7 | 4.5 |
| p-value (recovery rate) | >0.05 | >0.05 | >0.05 |
| structure | | | |
| Fold change | 5.5 | 3.6 | 7.2 |
| S.D. | 4.5 | 1.7 | 2.1 |
| p-value (recovery rate) | >0.05 | 0.02 | <0.01 |

As shown in the Table 4 above, Compounds A to Q exhibited activity that is about the same as Compound III-1 or higher than that of Compound III-1. Compounds H, P, and Q exhibited activity with a statistically significant differences in the recovery rate (splicing recovery effects of compound treatment where GFP/(GFP+RFP) of the solvent treated CFTRc. 3849+10kb mutant vector was set to 0% and GFP/(GFP+RFP) of the wild-type CFTR vector was 100%), and, in particular, Compounds H and Q exhibited higher activity values, compared to Compound III-1. Thus, the pseudo exon caused by the c.3849+10kb C>T mutation in the CFTR gene was suppressed by the above described compounds represented by Formula (IV), (VII), or (VIII), and as a result the normal CFTR splicing products was restored.

If a pseudo exon is produced within the intronic sequence of the CFTR gene, and the pseudo exon is included into mRNA, a premature stop codon is introduced for CFTR, resulting in functional and quantitative loss of CFTR. Thus, the compounds represented by Formulae (III), (IV), (VII), and (VIII) is expected to show therapeutic effect for cystic fibrosis by restoring normal splicing and functional production of CFTR.

Confirmation of Effect of Suppressing PTC Exon Recognition

A vector obtained by cloning target exon regions (COL4A5 gene exons 40, 41, and 42, and TSC2 gene exons 15, 16, and 17) for the COL4A5 gene (c.3710_3761del52 deletion mutation, PTC mutation) in Alport syndrome and the TSC2 gene (c.1783C>T, PTC mutation) in tuberous sclerosis was expressed in HeLa cells. Then the cells were treated with Compound III-1 (0 μM, 5 μM, 10 μM, 20 μM, 30 μM, and 50 μM) and induction of splicing alteration was verified through RT-PCR. Results thereof are shown in FIG. 7.

Figure 7A:
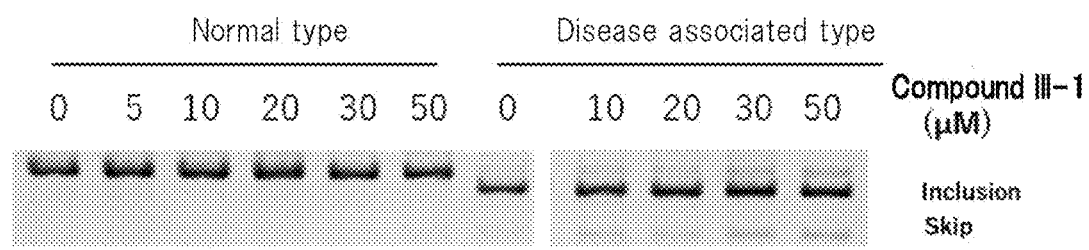
FIGS. 7A and 7B show one example of a functional isoform induction effect of administration of Compound III-1 on the COL4A5 gene in Alport syndrome and the TSC2 gene in tuberous sclerosis.
Figure 7B:
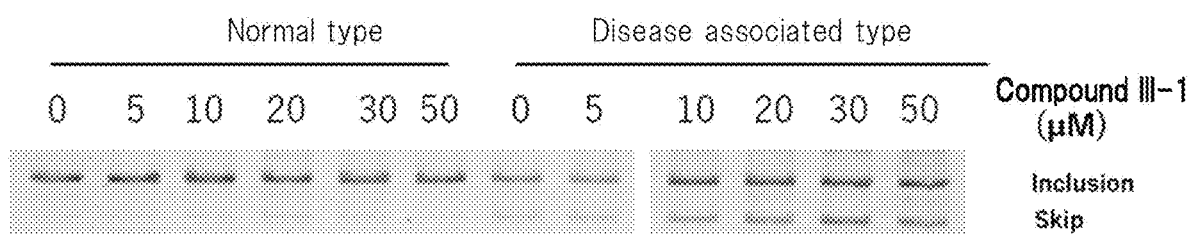

FIGS. 7A and 7B show examples of the results of RT-PCR on HeLa cells subjected to minigene transfection with the COL4A5 gene (FIG. 7A) in Alport syndrome, and the TSC2 gene (FIG. 7B) in tuberous sclerosis. As shown in FIGS. 7A and 7B, Compound III-1 had a concentration-dependent splicing induction effect on the COL4A5 gene and the TSC2 gene.

The invention claimed is:

1. A method for ameliorating, suppressing progression of, and/or treating a genetic disease caused by an aberrant splicing regulation, the method comprising administering a compound capable of suppressing a splicing abnormality that contributes to development or progression of the genetic diseases to a subject that requires the compound; wherein the disease is Fabry disease; and wherein the compound is a compound represented by Formula (X), or (X'), or a pharmaceutically acceptable salt thereof:

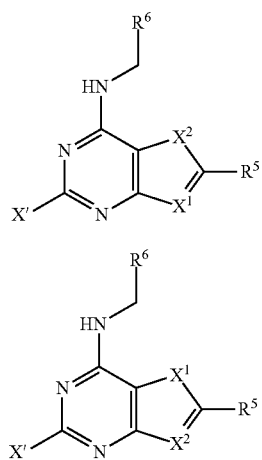

wherein R⁵ represents a hydrogen atom, a halogen atom, a methoxy group, or a 2,2,2-trifluoroethoxy group;

R⁶ represents a 2-furyl group, a 2-thiazolyl group, or a 4-pyridyl group;

X¹ represents N or CH;

X² represents NH, NCH₃, S, or O; and

X' represents a hydrogen atom, a chlorine atom, an iodine atom, a bromine atom, or a fluorine atom.

2. The method according to claim 1, wherein the compound is represented by Formula (X), or (X'), or a pharmaceutically acceptable salt thereof, wherein in Formulae (X) and (X'), R⁵ represents a hydrogen atom, a methoxy group, or a 2,2,2-trifluoroethoxy group;

X¹ represents N; and

X² represents NH.

3. The method according to claim 1, wherein the compound is selected from the group consisting of the following compounds:

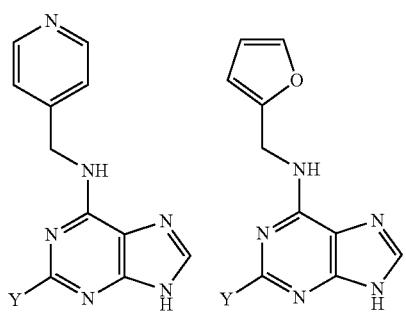

-continued

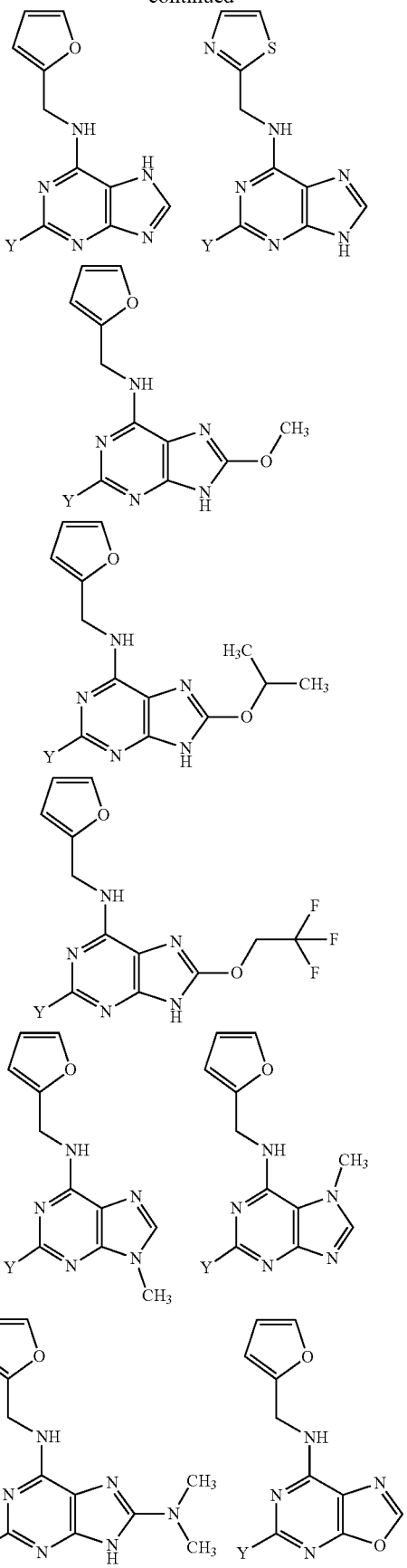

-continued
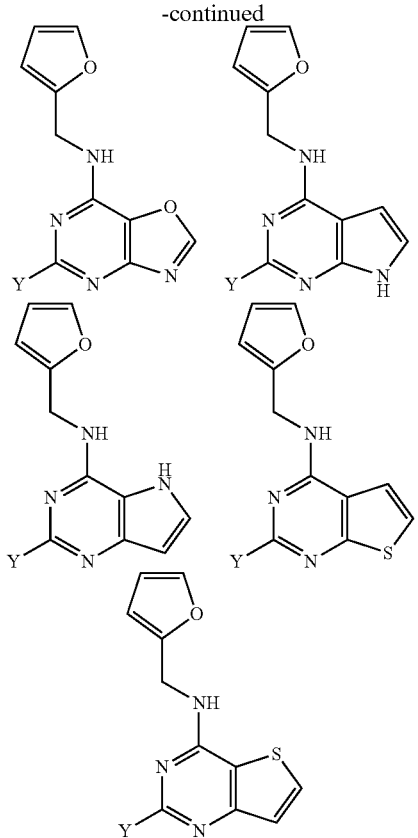
wherein Y represents a halogen atom.
4. The method according to claim 1, wherein the compound is:
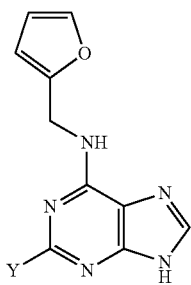
or
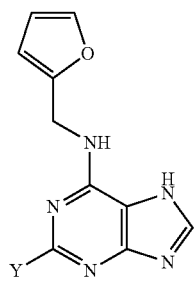
wherein Y represents a halogen atom.
5. The method according to claim 1, wherein the compound is selected from the group consisting of:
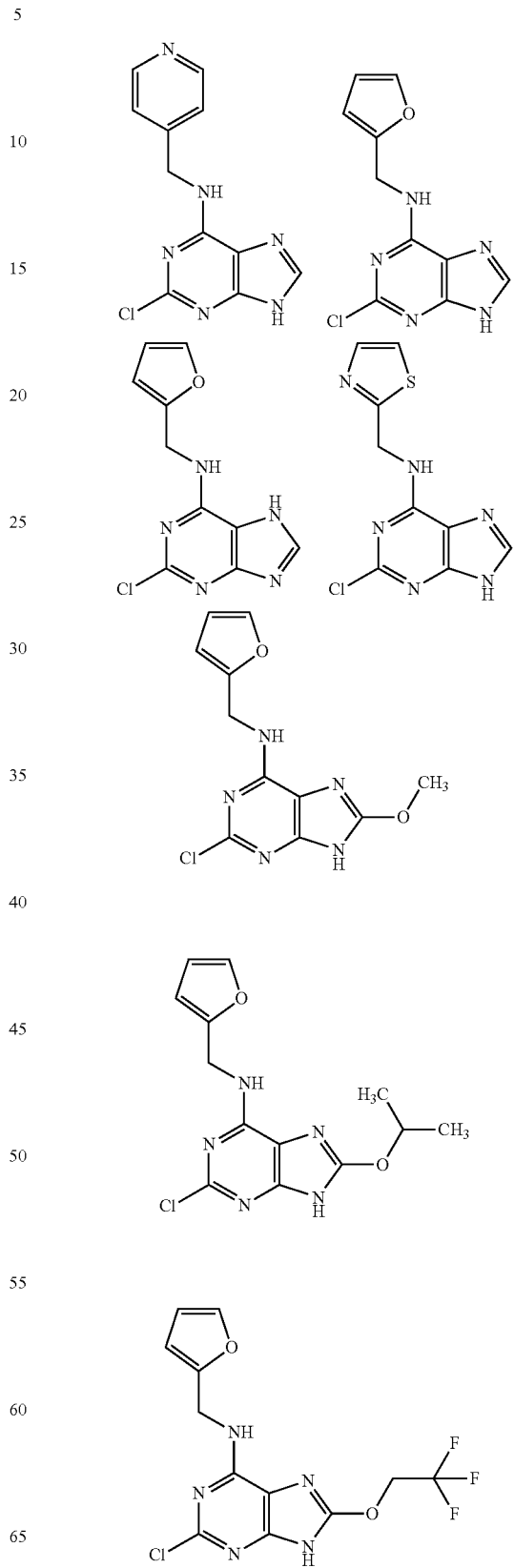

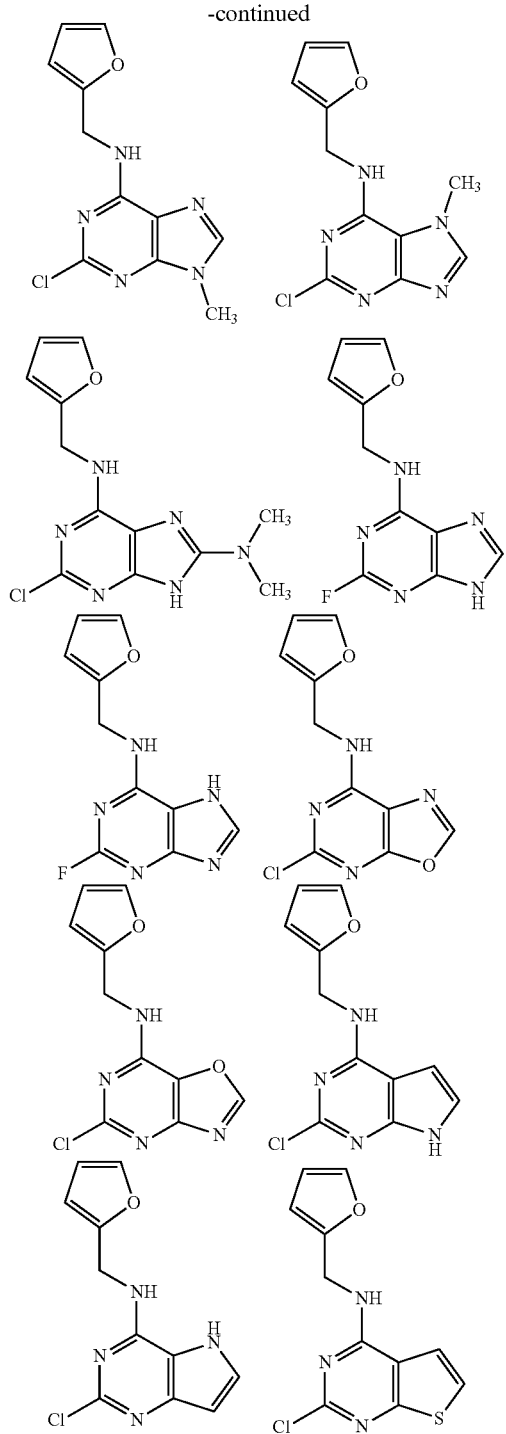
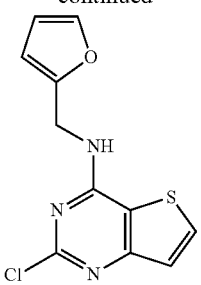
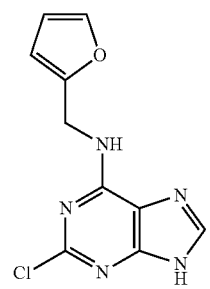 [SMILES: Clc1nc(NCc2ccco2)c2nc[nH]c2n1]
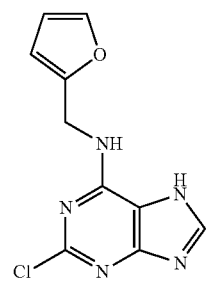 [SMILES: Clc1nc(NCc2ccco2)c2[nH]cnc2n1]
6. A method for treating a genetic disease caused by an aberrant splicing regulation, the method comprising administering to a subject in need thereof a compound is selected from the group consisting of the following compounds or a pharmaceutically acceptable salt of the compound:
or
wherein the disease is Fabry disease.
* * * * *